US007078037B2

(12) United States Patent
Galgiani et al.

(10) Patent No.: US 7,078,037 B2
(45) Date of Patent: Jul. 18, 2006

(54) **PEPTIDES AND DNA ENCODING THE PEPTIDES USEFUL FOR IMMUNIZATIONS AGAINST *COCCIDIOIDES* SPP. INFECTIONS**

(75) Inventors: John N. Galgiani, Tucson, AZ (US); Kris Orsborn, Tucson, AZ (US); Tao Peng, Tucson, AZ (US); Lisa Shubitz, Tucson, AZ (US)

(73) Assignee: The Arizona Board of Regents on Behalf of the University of Arizona, Tucson, AZ (US)

( * ) Notice: Subject to any disclaimer, the term of this patent is extended or adjusted under 35 U.S.C. 154(b) by 348 days.

(21) Appl. No.: 10/417,923

(22) Filed: Apr. 16, 2003

(65) Prior Publication Data

US 2004/0001843 A1 Jan. 1, 2004

Related U.S. Application Data

(60) Provisional application No. 60/373,635, filed on Apr. 19, 2002.

(51) Int. Cl.
*A61K 39/00* (2006.01)

(52) U.S. Cl. .............................. 424/185.1; 424/274.1; 435/975; 530/350

(58) Field of Classification Search ............. 424/185.1, 424/274.1; 435/975; 530/350
See application file for complete search history.

(56) References Cited

U.S. PATENT DOCUMENTS

| | | | |
|---|---|---|---|
| 5,284,747 | A | 2/1994 | Milliman |
| 5,622,827 | A | 4/1997 | McAllister et al. |
| 5,837,734 | A | 11/1998 | Bartsch et al. |

OTHER PUBLICATIONS

Ampel, Neil M., et al. (1992) "In Vitro Assessment of Cellular Immunity in Human Coccidioidomycosis: Relationship Between Dermal Hypersensitivity, Lymphocyte Transformation, and Lymphokine Production By Peripheral Blood Mononuclear Cells from Healthy Adults." *JID* 165:710-715.

Burgess, Wilson H., et al. (1990) "Possible Dissociation of the Heparin-Binding and Motegenic Activities of Heparin-Binding (Acidic Fibroblast) Growth Factor-1 from Its Receptor-Binding Activities by Site-Directed Mutagenesis of a Single Lysine Residue." *The Journal of Cell Biology* 111: 2129-2138.

Corry, David B., et al. (1996) "Cytokine Production of Peripheral Blood Mononuclear Cells in Human Coccidioidomycosis." *The Journal of Infectious Diseases* 174: 440-443.

Cox, Rebecca A., et al. "Vaccine Efficacy of *Coccidioides immitis* Antigen 2" Progress Report for Period Jan. 1, 1998-Dec. 31, 1999 pp. 1-11.

Franco, Manuel A., et al. (1993) "An Immunodominant Cytotoxic T Cell Epitope on the VP7 Rotavirus Protein Overlaps the H2 Signal Peptide." *Journal of General Virology* 74: 2579-2586.

Jobling, M. G., et al. (1991) "Analysis of Stucture and Function of the B Submit of Cholera Toxin by the Use of Site-Directed Mutagenesis." *Molecular Microbiology*, 5(7): 1755-1767.

Kondo, Tokukazu et al. (1995) "A Single Retroviral Gag Precursor Signal Peptide Recognized by FBL-3 Tumor-Specific Cytotoxic T Lymphocytes." *Journal of Virology*, vol. 69, No. 11, pp. 6735-3741.

Rudinger, J. "Characteristics of the Amino Acids as Components of a Peptide Hormone Sequence." Biological Council: The Co-ordinating Committee for Symposia on Drug Action: Peptide Hormones.

Stevens. David A. (1995) "Coccidioidomycisis" *Current Concepts*, vol. 332, No. 16, pp. 1077-1082.

Galgiani, John N., et al. (1992) "An Arthroconidial-Spherule Antigen of *Coccidioides immitis*: Differential Expression during In Vitro Fungal Development and Evidence for Humoral Response in Humans after Infection or Vaccination." *Infection and Immunity*, Jul. 1992, pp. 2627-2635.

Cox, Rebecca A., et al. (1993) "Production of a Murine Monoclonal Antibody That Recognizes an Epitope Specific to *Coccidioides immitis* Antigen 2." *Infection and Immunity*, May 1993, pp. 1895-1899.

Dugger, Kris Orsborn. Et al. (1996) "Cloning and Sequence Analysis of the cDNA for a protein from *Coccidioides immitis* with Immunogenic Potential." *Biochemical and Biophysical Research Communications* 218, pp. 485-489 (1996).

Kirkland, Theo N., et al. (1998) "Evaluation of the Proline-Rich Antigen of *Coccidioides immitis* as a Vaccine Candidate in Mice." *Infection and Immunity*, Aug. 1998 pp. 3519-3522.

Orsborn, Kris I., et al. (1998) "Detecting Serum Antibodies to a Purified Recombinant Proline-Rich Antigen of *Coccidioides immitis* in Patients with Coccidioidomycosis." *Clinical Infections Diseases*, 27:1475-1478.

Peng, Tao et al., (1999) "Proline-Rich Vaccine Candidate Antigen of *Coccidioides immitis*: Conservation among Isolates and Differential Expression with Spherule Maturation." *The Journal of Infectiontious Diseases*, 179:518-521.

(Continued)

*Primary Examiner*—Mark Navarro
(74) *Attorney, Agent, or Firm*—Morrison & Foerster LLP

(57) ABSTRACT

The present invention provides compositions of peptides and polynucleotides encoding the peptides, which peptides are useful for generating an immunological response in an individual and in therapeutic and diagnostic applications of infections due to pathogenic *Coccidioides* spp. fungi, such as *C. immitis* or *C. posadasii.*

18 Claims, 5 Drawing Sheets

OTHER PUBLICATIONS

Abuodeh, Rahed O., et al. (1999) "Resistance to *Coccidioides immitis* in Mice after Immunization with Recombinant Protein or a DNA Vaccine of a Proline-Rich Antigen." *Infection and Immunity*, Jun. 1999, pp. 2935-2940.

Shubitz, Lisa et al. (2002) "Protection of Mice against *Coccidioides immitis* Intranasal Infection by Vaccination with Recombinant Antigen 2/PRA." *Infections and Immunity*, Jun. 2002, pp. 3287-3289.

Peng, Tao et al. (2002) "Localization within a Proline-Rich Antigen (Ag2/PRA0 of protective Antigenicity against Infection with *Coccidioides immitis* in Mice." *Infection and Immunity*, Jul. 2002, pp. 3330-3335.

Dugger, Orsborn K., et al. (1995) "Cloning and Partial Sequence of a 33 kDA Protein Antigen from *Coccidioides immitis." American Society for Microbiology, 95th General Meeting Washington, DC.* May 21-25, 1995.

Peng, T., et al. (1997) "Cloning and Sequence Analysis of the Complete Gene for the Proline Rich Antigen of *Coccidioides immitis." American Society for Microbiology, 97th General Meeting Miami Beach.* May 4-8, 1997.

Orsborn, K. I., et al. (1997) "Expression of a Proline Rich Antigen (PRA0 from *Coccidioides immitis* as a Potential Immunodiagnostic Reagent." *American Society for Microbiology, 97th General Meeting Miami Beach.* May 4-8, 1997.

Sigel, E. M., et al. (1997) "DNA Vaccinations of Mice to Immunize against *Coccidioides immitis." Clinical Infectious Disease*, 25(2): 357.

Abuodeh, R. O., et al. (1999) "A Recombinant Proline Rich Antigen (rPRA) Protein and its Cloned Gene from *Coccidioides immitis* as Vaccines." ASM 99th General Meeting, Chicago, IL.

Peng, T., et al. (2001) "Contribution to Protection by Different Domains of Ag2/PRA, a Candidate Vaccine Against *Coccidioides immitis." Session No. 132/F. Abstract F-67.* May, 22, 2001.

Peng, T., et al. (2001) "10 Recent Studies of Antigen 2/PRA." *Proceedings of the Annual Coccidiodomycosis Study Group Meeting.* Mar. 31, 2001.

Pan, Shuchong et al. (1995) "Molecular and Biochemical Characterization of a *Coccidioides immitis*-Specific Antigen." *Infection and Immunity*, Oct. 1995, pp. 3994-4002.

Cole, Garry et al. (1989) "Isolation of Antigens with Proteolytic Activity from *Coccidioides immitis*." *Infection and Immunity*, May 1989, pp. 1524-1534.

Cole, G. T., et al. (1986) "Antigen Identification in *Coccidioides immitis*." *Microbiology 1986 American Society of Microbiology*, pp. 159-164.

Pan, S., (1994) "The Gene and Primary Structure of a Putative *Coccidioides immitis*-Specific (CS) Antigen." *94th ASM General Meeting*, May 22-27, 1994.

Jiang. Chengyong et al. (2002) "Role of Signal Sequence in Vaccine-Induced Protection against Experimental Coccidioidomycosis" *Infection and Immunity* 70 (7): 3539-3545.

Zhu, Yufan et al. (1996) "Molecular Cloning and Characterization of *Coccidioides immitis* Antigen 2cDNA" *Infection and Immunity* 64 (7): 2695-2699.

Cox, Rebecca A. et al "Vaccine Efficacy *Coccidioides immitis* Antigen 2." Progress Report Submitted to California State Bakersfield Foundation, Valley Fever Vaccine Project Meeting. Report for Period Jan. 1, 2000-Jun. 31, 2000.

Cox, Rebecca A. et al "Vaccine Efficacy *Coccidioides immitis* Antigen 2." Progress Report Submitted to California State Bakersfield Foundation, Valley Fever Vaccine Project Meeting. Report for Period Jul. 1, 2000-Dec. 31, 2000.

Zhu, Yufan et al. (1996) "*Coccidioides immitis* Antigen 2: Analysis of Gene and Protein." *Gene* 181:121-125.

Zhu, Yufan et al. (1996) "Identification of a *Coccidioides immitis* Antigen 2 Domain That Express B- Cell-Reactive Epitopes." *Infection and Immunity* 65 (8): 3376-3380, 1997.

Jiang et al. "Genetic Vaccination Against *Coccidioides immitis*: Comparison of Vaccine Efficacy of Recombinant Antigen 2 and Antigen cDNA." Infec. Immun. 67(2):630-635, 1999.

Figure 1. Nucleotide (Genbank Accession number U39835; SEQ. ID NO:1) and deduced amino acid sequence (SEQ ID NO: 2) of Ag2/PRA1-194 aligned by the TRANSLATE program of the GCG Package.

```
   1  agttatttc cttccccata taaaaacata cattcgttc gtggtccatc aaagactatc
  61  gttaattctc caaccccggt tgtcgttttt tttggtgtac tattagggag gataatcgtt
 121  ctcgtccgtt agacgcacat acataatcaa aatgcagttc tctcacgctc tcatcgctct
                                        M  Q  F   S  H  A   L  I  A

 181  cgtcgctgcc ggcctcgcca gtgcccagct cccagacatc ccaccttgcg ctctcaactg
      L  V  A  A   G  L  A   S  A  Q   L  P  D  I   P  P  C   A  L  N

 241  cttcgttgag gctctcggca acgatggctg cactcgcttg accgacttca agtgccactg
      C  F  V  E   A  L  G   N  D  G   C  T  R  L   T  D  F   K  C  H

 301  ctccaagcct gagctcccag gacagatcac tccttgcgtt gaggaggcct gccctctcga
      C  S  K  P   E  L  P   G  Q  I   T  P  C  V   E  E  A   C  P  L

 361  cgcccgtatc tccgtctcca acatcgtcgt tgaccagtgc tccaaggccg gtgtcccaat
      D  A  R  I   S  V  S   N  I  V   V  D  Q  C   S  K  A   G  V  P

 421  tgacatccca ccagttgaca ccaccgccgc tcccgagcca tccgagaccg ctgagcccac
      I  D  I  P   P  V  D   T  T  A   A  P  E  P   S  E  T   A  E  P

 481  cgctgagcca accgaggagc ccactgccga gcctaccgct gagcccaccg ctgagccgac
      T  A  E  P   T  E  E   P  T  A   E  P  T  A   E  P  T   A  E  P

 541  tcatgagccc accgaggagc ccactgccgt cccaaccggc actggcggtg gtgtccccac
      T  H  E  P   T  E  E   P  T  A   V  P  T  G   T  G  G   G  V  P

 601  tggcaccggt tccttcaccg tcactggcag accaactgcc tccaccccag ctgagttccc
      T  G  T  G   S  F  T   V  T  G   R  P  T  A   S  T  P   A  E  F

 661  aggtgctggc tccaacgtcc gtgccagcgt tggcggcatt gctgctgctc tcctcggtct
      P  G  A  G   S  N  V   R  A  S   V  G  G  I   A  A  A   L  L  G

 721  cgctgcctac ctgtaaattt agactatcag caaaactgac aagcacgtcg ccatggcgtc
      L  A  A  Y   L  -

 781  aattattccc cccgcgcatt tttcccagtt catttttttc tcgacaacaa ttcagcacgc
 841  attggaaggc gaaatgaccc ggatgtccgc aacacgataa aagtttcacg atctctcttc
 901  tctgctctcc cctctctggg aggctctaag tttcatttgg attgaaatgg ggcgatgggc
 961  aatcgttcgt tgggggtgaa gggagtgggg atctgggatt cgggattccc gaaagtcaaa
1021  aacgctttat tctgcgatgt gaccacggct atgggtgtac aatgttgtgt ctgtgacttt
1081  tttacggggg gggagaaacg aatataacac acctgatttc acttcacact tattacttat
1141  cctgtatcta attgacatct gggaaaggga gcttatttcc ctgttaataa tttggtgtta
1201  t
```

Figure 2. Nucleotide (SEQ ID NO:3) and deduced amino acid sequence (SEQ ID NO:4) for recombinant Ag2/PRA1-106 expressed in an *E. coli* host.

```
  1  atgagcgata aaattattca cctgactgac gacagttttg acacggatgt actcaaagcg
       M  S  D   K  I  I   H  L  T  D   D  S  F   D  T  D   V  L  K  A

 61  gacggggcga tcctcgtcga tttctgggca gagtggtgcg gtccgtgcaa aatgatcgcc
       D  G  A   I  L  V   D  F  W  A   E  W  C   G  P  C   K  M  I  A

121  ccgattctgg atgaaatcgc tgacgaatat cagggcaaac tgaccgttgc aaaactgaac
       P  I  L   D  E  I   A  D  E  Y   Q  G  K   L  T  V   A  K  L  N

181  atcgatcaaa accctggcac tgcgccgaaa tatggcatcc gtggtatccc gactctgctg
       I  D  Q   N  P  G   T  A  P  K   Y  G  I   R  G  I   P  T  L  L

241  ctgttcaaaa acggtgaagt ggcggcaacc aaagtgggtg cactgtctaa aggtcagttg
       L  F  K   N  G  E   V  A  A  T   K  V  G   A  L  S   K  G  Q  L

301  aaagagttcc tcgacgctaa cctggccggt tctggttctg gccatatgca ccatcatcat
       K  E  F   L  D  A   N  L  A  G   S  G  S   G  H  M   H  H  H  H

361  catcattctt ctggtctggt gccacgcggt tctggtatga aagaaaccgc tgctgctaaa
       H  H  S   S  G  L   V  P  R  G   S  G  M   K  E  T   A  A  A  K

421  ttcgaacgcc agcacatgga cagcccagat ctgggtaccg acgacgacga caaggccatg
       F  E  R   Q  H  M   D  S  P  D   L  G  T   D  D  D   D  K  A  M

481  gctgatatcg gatccatgca gttctctcac gctctcatcg ctctcgtcgc tgccggcctc
       A  D  I   G  S  M   Q  F  S  H   A  L  I   A  L  V   A  A  G  L

541  gccagtgccc agctcccaga catcccacct tgcgctctca actgcttcgt tgaggctctc
       A  S  A   Q  L  P   D  I  P  P   C  A  L   N  C  F   V  E  A  L

601  ggcaacgatg gctgcactcg cttgaccgac ttcaagtgcc actgctccaa gcctgagctc
       G  N  D   G  C  T   R  L  T  D   F  K  C   H  C  S   K  P  E  L

661  ccaggacaga tcactccttg cgttgaggag gcctgccctc tcgacgcccg tatctccgtc
       P  G  Q   I  T  P   C  V  E  E   A  C  P   L  D  A   R  I  S  V

721  tccaacatcg tcgttgacca gtgctccaag gccggtgtcc caattgacat cccaccagtt
       S  N  I   V  V  D   Q  C  S  K   A  G  V   P  I  D   I  P  P  V

781  gacaccaccg ccgctcccga gccatccgag acctaa
       D  T  T   A  A  P   E  P  S  E   T  -
```

Figure 3. Nucleotide (SEQ ID NO:6) and deduced amino acid sequence (SEQ ID NO:7) of recombinant Ag2/PRA27-106.

```
  1  atgggcagca gccatcatca tcatcatcac agcagcggcc tggtgccgcg cggcagccat
        M  G  S   S  H  H   H  H  H  H   S  S  G   L  V  P   R  G  S  H

 61  atggctagca tgactggtgg acagcaaatg ggtcgcggat ccgctctcaa ctgcttcgtt
        M  A  S   M  T  G   G  Q  Q  M   G  R  G   S  A  L   N  C  F  V

121  gaggctctcg gcaacgatgg ctgcactcgc ttgaccgact tcaagtgcca ctgctccaag
        E  A  L   G  N  D   G  C  T  R   L  T  D   F  K  C   H  C  S  K

181  cctgagctcc caggacagat cactccttgc gttgaggagg cctgccctct cgacgcccgt
        P  E  L   P  G  Q   I  T  P  C   V  E  E   A  C  P   L  D  A  R

241  atctccgtct ccaacatcgt cgttgaccag tgctccaagg ccggtgtccc aattgacatc
        I  S  V   S  N  I   V  V  D  Q   C  S  K   A  G  V   P  I  D  I

301  ccaccagttg acaccaccgc cgctcccgag ccatccgaga cctaa
        P  P  V   D  T  T   A  A  P  E   P  S  E   T  -
```

Figure 4. Nucletide (SEQ ID NO:8) and deduced amino acid sequence (SEQ ID NO:9) of recombinant Ag2/PRA1-106 expressed in *Saccharomyces cerevisiae*.

```
  1  gactacaagg atgacgatga caaggaattc ctcgagcccg ggagatctat cgatggatcc
      D  Y  K   D  D  D   D  K  E  F   L  E  P   G  R  S   I  D  G  S

 61  atgcagttct ctcacgctct catcgctctc gtcgctgccg gcctcgccag tgcccagctc
      M  Q  F   S  H  A   L  I  A  L   V  A  A   G  L  A   S  A  Q  L

121  ccagacatcc caccttgcgc tctcaactgc ttcgttgagg ctctcggcaa cgatggctgc
      P  D  I   P  P  C   A  L  N  C   F  V  E   A  L  G   N  D  G  C

181  actcgcttga ccgacttcaa gtgccactgc tccaagcctg agctcccagg acagatcact
      T  R  L   T  D  F   K  C  H  C   S  K  P   E  L  P   G  Q  I  T

241  ccttgcgttg aggaggcctg ccctctcgac gcccgtatct ccgtctccaa catcgtcgtt
      P  C  V   E  E  A   C  P  L  D   A  R  I   S  V  S   N  I  V  V

301  gaccagtgct ccaaggccgg tgtcccaatt gacatcccac cagttgacac caccgccgct
      D  Q  C   S  K  A   G  V  P  I   D  I  P   P  V  D   T  T  A  A

361  cccgagccat ccgagaccta a
      P  E  P   S  E  T   -
```

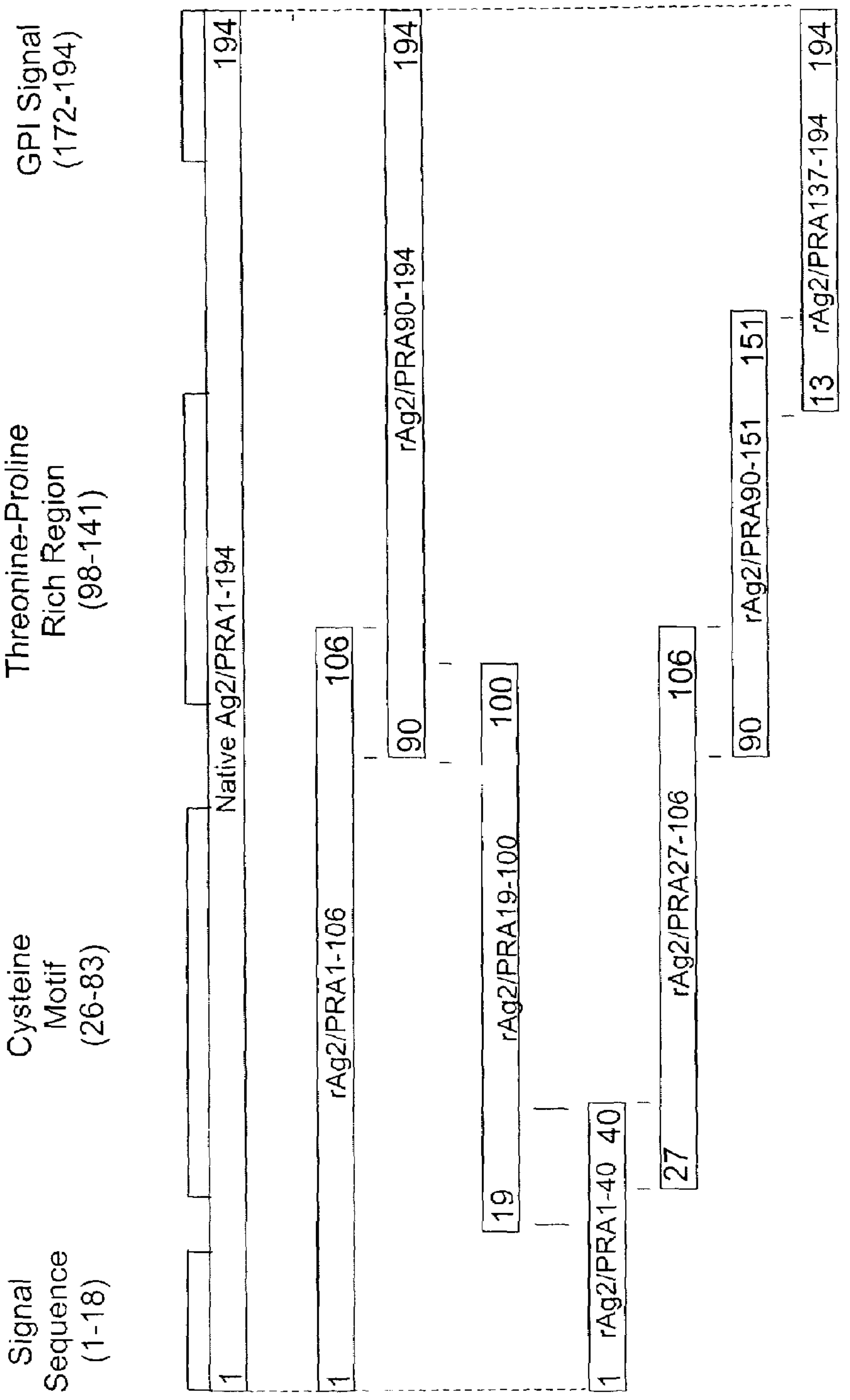
Figure 5. Full-length and truncated polypeptides of Ag2/PRA

SEQUENCE LISTING

<160> NUMBER OF SEQ ID NOS: 35

<210> SEQ ID NO 1
<211> LENGTH: 1201
<212> TYPE: DNA
<213> ORGANISM: Coccidioides posadasii

<400> SEQUENCE: 1
agttattttc cttccccata taaaaacata cattcgtttc gtggtccatc aaagactatc 60
gttaattctc caaccccggt tgtcgttttt tttggtgtac tattagggag gataatcgtt 120
ctcgtccgtt agacgcacat acataatcaa aatgcagttc tctcacgctc tcatcgctct 180
cgtcgctgcc ggcctcgcca gtgcccagct cccagacatc ccaccttgcg ctctcaactg 240
cttcgttgag gctctcggca acgatggctg cactcgcttg accgacttca agtgccactg 300
ctccaagcct gagctcccag gacagatcac tccttgcgtt gaggaggcct gccctctcga 360
cgcccgtatc tccgtctcca acatcgtcgt tgaccagtgc tccaaggccg gtgtcccaat 420
tgacatccca ccagttgaca ccaccgccgc tcccgagcca tccgagaccg ctgagcccac 480
cgctgagcca accgaggagc ccactgccga gcctaccgct gagcccaccg ctgagccgac 540
tcatgagccc accgaggagc ccactgccgt cccaaccggc actggcggtg gtgtccccac 600
tggcaccggt tccttcaccg tcactggcag accaactgcc tccaccccag ctgagttccc 660
aggtgctggc tccaacgtcc gtgccagcgt tggcggcatt gctgctgctc tcctcggtct 720
cgctgcctac ctgtaaattt agactatcag caaaactgac aagcacgtcg ccatggcgtc 780
aattattccc cccgcgcatt tttcccagtt cattttttc tcgacaacaa ttcagcacgc 840
attggaaggc gaaatgaccc ggatgtccgc aacacgataa aagtttcacg atctctcttc 900
tctgctctcc cctctctggg aggctctaag tttcatttgg attgaaatgg ggcgatgggc 960
aatcgttcgt tgggggtgaa gggagtgggg atctgggatt cgggattccc gaaagtcaaa 1020
aacgctttat tctgcgatgt gaccacggct atgggtgtac aatgttgtgt ctgtgacttt 1080
tttacggggg gggagaaacg aatataacac acctgatttc acttcacact tattacttat 1140
cctgtatcta attgacatct gggaaaggga gcttatttcc ctgttaataa tttggtgtta 1200
t 1201

<210> SEQ ID NO 2
<211> LENGTH: 194
<212> TYPE: PRT
<213> ORGANISM: Coccidioides posadasii

<400> SEQUENCE: 2

Met Gln Phe Ser His Ala Leu Ile Ala Leu Val Ala Ala Gly Leu Ala
1 5 10 15

Ser Ala Gln Leu Pro Asp Ile Pro Pro Cys Ala Leu Asn Cys Phe Val
20 25 30

-continued

```
Glu Ala Leu Gly Asn Asp Gly Cys Thr Arg Leu Thr Asp Phe Lys Cys
        35                  40                  45

His Cys Ser Lys Pro Glu Leu Pro Gly Gln Ile Thr Pro Cys Val Glu
    50                  55                  60

Glu Ala Cys Pro Leu Asp Ala Arg Ile Ser Val Ser Asn Ile Val Val
65                  70                  75                  80

Asp Gln Cys Ser Lys Ala Gly Val Pro Ile Asp Ile Pro Pro Val Asp
                85                  90                  95

Thr Thr Ala Ala Pro Glu Pro Ser Glu Thr Ala Glu Pro Thr Ala Glu
            100                 105                 110

Pro Thr Glu Glu Pro Thr Ala Glu Pro Thr Ala Glu Pro Thr Ala Glu
        115                 120                 125

Pro Thr His Glu Pro Thr Glu Glu Pro Thr Ala Val Pro Thr Gly Thr
    130                 135                 140

Gly Gly Gly Val Pro Thr Gly Thr Gly Ser Phe Thr Val Thr Gly Arg
145                 150                 155                 160

Pro Thr Ala Ser Thr Pro Ala Glu Phe Pro Gly Ala Gly Ser Asn Val
                165                 170                 175

Arg Ala Ser Val Gly Gly Ile Ala Ala Ala Leu Leu Gly Leu Ala Ala
            180                 185                 190

Tyr Leu
```

<210> SEQ ID NO 3
<211> LENGTH: 816
<212> TYPE: DNA
<213> ORGANISM: Artificial Sequence
<220> FEATURE:
<223> OTHER INFORMATION: Recombinant construct

<400> SEQUENCE: 3

```
atgagcgata aaattattca cctgactgac gacagttttg acacggatgt actcaaagcg     60

gacggggcga tcctcgtcga tttctgggca gagtggtgcg gtccgtgcaa aatgatcgcc    120

ccgattctgg atgaaatcgc tgacgaatat cagggcaaac tgaccgttgc aaaactgaac    180

atcgatcaaa accctggcac tgcgccgaaa tatggcatcc gtggtatccc gactctgctg    240

ctgttcaaaa acggtgaagt ggcggcaacc aaagtgggtg cactgtctaa aggtcagttg    300

aaagagttcc tcgacgctaa cctggccggt tctggttctg gccatatgca ccatcatcat    360

catcattctt ctggtctggt gccacgcggt tctggtatga aagaaaccgc tgctgctaaa    420

ttcgaacgcc agcacatgga cagcccagat ctgggtaccg acgacgacga caaggccatg    480

gctgatatcg gatccatgca gttctctcac gctctcatcg ctctcgtcgc tgccggcctc    540

gccagtgccc agctcccaga catcccacct tgcgctctca actgcttcgt tgaggctctc    600

ggcaacgatg gctgcactcg cttgaccgac ttcaagtgcc actgctccaa gcctgagctc    660

ccaggacaga tcactccttg cgttgaggag gcctgccctc tcgacgcccg tatctccgtc    720

tccaacatcg tcgttgacca gtgctccaag gccggtgtcc caattgacat cccaccagtt    780

gacaccaccg ccgctcccga gccatccgag acctaa                              816
```

<210> SEQ ID NO 4
<211> LENGTH: 271
<212> TYPE: PRT
<213> ORGANISM: Artificial Sequence
<220> FEATURE:
<223> OTHER INFORMATION: Fusion peptide -continued

<400> SEQUENCE: 4

```
Met Ser Asp Lys Ile Ile His Leu Thr Asp Asp Ser Phe Asp Thr Asp
 1               5                  10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Asp Lys Ala Met
145                 150                 155                 160

Ala Asp Ile Gly Ser Met Gln Phe Ser His Ala Leu Ile Ala Leu Val
                165                 170                 175

Ala Ala Gly Leu Ala Ser Ala Gln Leu Pro Asp Ile Pro Pro Cys Ala
            180                 185                 190

Leu Asn Cys Phe Val Glu Ala Leu Gly Asn Asp Gly Cys Thr Arg Leu
        195                 200                 205

Thr Asp Phe Lys Cys His Cys Ser Lys Pro Glu Leu Pro Gly Gln Ile
    210                 215                 220

Thr Pro Cys Val Glu Glu Ala Cys Pro Leu Asp Ala Arg Ile Ser Val
225                 230                 235                 240

Ser Asn Ile Val Val Asp Gln Cys Ser Lys Ala Gly Val Pro Ile Asp
                245                 250                 255

Ile Pro Pro Val Asp Thr Thr Ala Ala Pro Glu Pro Ser Glu Thr
            260                 265                 270
```

<210> SEQ ID NO 5
<211> LENGTH: 142
<212> TYPE: PRT
<213> ORGANISM: Artificial Sequence
<220> FEATURE:
<223> OTHER INFORMATION: Fusion peptide

<400> SEQUENCE: 5

```
Gly Ser Gly Met Lys Glu Thr Ala Ala Ala Lys Phe Glu Arg Gln His
 1               5                  10                  15

Met Asp Ser Pro Asp Leu Gly Thr Asp Asp Asp Asp Lys Ala Met Ala
            20                  25                  30

Asp Ile Gly Ser Met Gln Phe Ser His Ala Leu Ile Ala Leu Val Ala
        35                  40                  45

Ala Gly Leu Ala Ser Ala Gln Leu Pro Asp Ile Pro Pro Cys Ala Leu
    50                  55                  60

Asn Cys Phe Val Glu Ala Leu Gly Asn Asp Gly Cys Thr Arg Leu Thr
65                  70                  75                  80
```

-continued

```
Asp Phe Lys Cys His Cys Ser Lys Pro Glu Leu Pro Gly Gln Ile Thr
                85                  90                  95

Pro Cys Val Glu Glu Ala Cys Pro Leu Asp Ala Arg Ile Ser Val Ser
            100                 105                 110

Asn Ile Val Val Asp Gln Cys Ser Lys Ala Gly Val Pro Ile Asp Ile
        115                 120                 125

Pro Pro Val Asp Thr Thr Ala Ala Pro Glu Pro Ser Glu Thr
    130                 135                 140
```

<210> SEQ ID NO 6
<211> LENGTH: 345
<212> TYPE: DNA
<213> ORGANISM: Artificial Sequence
<220> FEATURE:
<223> OTHER INFORMATION: Recombinant construct

<400> SEQUENCE: 6

```
atgggcagca gccatcatca tcatcatcac agcagcggcc tggtgccgcg cggcagccat     60

atggctagca tgactggtgg acagcaaatg ggtcgcggat ccgctctcaa ctgcttcgtt    120

gaggctctcg gcaacgatgg ctgcactcgc ttgaccgact tcaagtgcca ctgctccaag    180

cctgagctcc caggacagat cactccttgc gttgaggagg cctgccctct cgacgcccgt    240

atctccgtct ccaacatcgt cgttgaccag tgctccaagg ccggtgtccc aattgacatc    300

ccaccagttg acaccaccgc cgctcccgag ccatccgaga cctaa                    345
```

<210> SEQ ID NO 7
<211> LENGTH: 114
<212> TYPE: PRT
<213> ORGANISM: Artificial Sequence
<220> FEATURE:
<223> OTHER INFORMATION: Fusion peptide

<400> SEQUENCE: 7

```
Met Gly Ser Ser His His His His His His Ser Ser Gly Leu Val Pro
 1               5                  10                  15

Arg Gly Ser His Met Ala Ser Met Thr Gly Gly Gln Gln Met Gly Arg
            20                  25                  30

Gly Ser Ala Leu Asn Cys Phe Val Glu Ala Leu Gly Asn Asp Gly Cys
        35                  40                  45

Thr Arg Leu Thr Asp Phe Lys Cys His Cys Ser Lys Pro Glu Leu Pro
    50                  55                  60

Gly Gln Ile Thr Pro Cys Val Glu Glu Ala Cys Pro Leu Asp Ala Arg
65                  70                  75                  80

Ile Ser Val Ser Asn Ile Val Val Asp Gln Cys Ser Lys Ala Gly Val
                85                  90                  95

Pro Ile Asp Ile Pro Pro Val Asp Thr Thr Ala Ala Pro Glu Pro Ser
            100                 105                 110

Glu Thr
```

<210> SEQ ID NO 8
<211> LENGTH: 381
<212> TYPE: DNA
<213> ORGANISM: Artificial Sequence
<220> FEATURE:
<223> OTHER INFORMATION: Recombinant construct -continued

<400> SEQUENCE: 8

```
gactacaagg atgacgatga caaggaattc ctcgagcccg ggagatctat cgatggatcc     60
atgcagttct ctcacgctct catcgctctc gtcgctgccg gcctcgccag tgcccagctc    120
ccagacatcc caccttgcgc tctcaactgc ttcgttgagg ctctcggcaa cgatggctgc    180
actcgcttga ccgacttcaa gtgccactgc tccaagcctg agctcccagg acagatcact    240
ccttgcgttg aggaggcctg ccctctcgac gcccgtatct ccgtctccaa catcgtcgtt    300
gaccagtgct ccaaggccgg tgtcccaatt gacatcccac cagttgacac caccgccgct    360
cccgagccat ccgagaccta a                                              381
```

<210> SEQ ID NO 9
<211> LENGTH: 126
<212> TYPE: PRT
<213> ORGANISM: Artificial Sequence
<220> FEATURE:
<223> OTHER INFORMATION: Fusion peptide

<400> SEQUENCE: 9

```
Asp Tyr Lys Asp Asp Asp Asp Lys Glu Phe Leu Glu Pro Gly Arg Ser
 1               5                  10                  15

Ile Asp Gly Ser Met Gln Phe Ser His Ala Leu Ile Ala Leu Val Ala
            20                  25                  30

Ala Gly Leu Ala Ser Ala Gln Leu Pro Asp Ile Pro Pro Cys Ala Leu
        35                  40                  45

Asn Cys Phe Val Glu Ala Leu Gly Asn Asp Gly Cys Thr Arg Leu Thr
    50                  55                  60

Asp Phe Lys Cys His Cys Ser Lys Pro Glu Leu Pro Gly Gln Ile Thr
65                  70                  75                  80

Pro Cys Val Glu Glu Ala Cys Pro Leu Asp Ala Arg Ile Ser Val Ser
                85                  90                  95

Asn Ile Val Val Asp Gln Cys Ser Lys Ala Gly Val Pro Ile Asp Ile
            100                 105                 110

Pro Pro Val Asp Thr Thr Ala Ala Pro Glu Pro Ser Glu Thr
        115                 120                 125
```

<210> SEQ ID NO 10
<211> LENGTH: 795
<212> TYPE: DNA
<213> ORGANISM: Artificial Sequence
<220> FEATURE:
<223> OTHER INFORMATION: Recombinant construct

<400> SEQUENCE: 10

```
gactacaagg atgacgatga caaggaattc atgcagttct ctcacgctct catcgctctc     60
gtcgctgccg gcctcgccag tgcccagctc ccagacatcc caccttgcgc tctcaactgc    120
ttcgttgagg ctctcggcaa cgatggctgc actcgcttga ccgacttcaa gtgccactgc    180
tccaagcctg agctcccagg acagatcact ccttgcgttg aggaggcctg ccctctcgac    240
gcccgtatct ccgtctccaa catcgtcgtt gaccagtgct ccaaggccgg tgtcccaatt    300
gacatcccac cagttgacac caccgccgct cccgagccat ccgagaccgg atccatgaag    360
ttctcactcc tcagcgctat cgcagcggct gtcttcgtcc ctttcacatc cgccactcca    420
cttgctagca cggccgacct cagctacgac actcactacg atgacccatc cctgcccctg    480
agtggcgtca cctgttctga cggggacaat ggcatgataa caaagggcta caacaccgcc    540
ggcgagatac caaactaccc tcacgtcgga ggagctttta cggtcgaaac gtggaacagc    600
```

-continued cccaactgtg gaaagtgcta caaagtgaca tacaatgcta aaacgatttt tttgactgcg 660
atcgaccaca gcaactccgg atttaatatc gcgaagaagt cgatggacgt attgacgaac 720
ggacgggcag aggaattggg caggatcaag gtgacctacg aagaggtcgc ctcgtcgttg 780
tgcgggttga aataa 795

<210> SEQ ID NO 11
<211> LENGTH: 264
<212> TYPE: PRT
<213> ORGANISM: Artificial Sequence
<220> FEATURE:
<223> OTHER INFORMATION: Fusion peptide

<400> SEQUENCE: 11

Asp Tyr Lys Asp Asp Asp Asp Lys Glu Phe Met Gln Phe Ser His Ala
1 5 10 15

Leu Ile Ala Leu Val Ala Ala Gly Leu Ala Ser Ala Gln Leu Pro Asp
20 25 30

Ile Pro Pro Cys Ala Leu Asn Cys Phe Val Glu Ala Leu Gly Asn Asp
35 40 45

Gly Cys Thr Arg Leu Thr Asp Phe Lys Cys His Cys Ser Lys Pro Glu
50 55 60

Leu Pro Gly Gln Ile Thr Pro Cys Val Glu Glu Ala Cys Pro Leu Asp
65 70 75 80

Ala Arg Ile Ser Val Ser Asn Ile Val Val Asp Gln Cys Ser Lys Ala
85 90 95

Gly Val Pro Ile Asp Ile Pro Pro Val Asp Thr Thr Ala Ala Pro Glu
100 105 110

Pro Ser Glu Thr Gly Ser Met Lys Phe Ser Leu Leu Ser Ala Ile Ala
115 120 125

Ala Ala Val Phe Val Pro Phe Thr Ser Ala Thr Pro Leu Ala Ser Thr
130 135 140

Ala Asp Leu Ser Tyr Asp Thr His Tyr Asp Asp Pro Ser Leu Pro Leu
145 150 155 160

Ser Gly Val Thr Cys Ser Asp Gly Asp Asn Gly Met Ile Thr Lys Gly
165 170 175

Tyr Asn Thr Ala Gly Glu Ile Pro Asn Tyr Pro His Val Gly Gly Ala
180 185 190

Phe Thr Val Glu Thr Trp Asn Ser Pro Asn Cys Gly Lys Cys Tyr Lys
195 200 205

Val Thr Tyr Asn Ala Lys Thr Ile Phe Leu Thr Ala Ile Asp His Ser
210 215 220

Asn Ser Gly Phe Asn Ile Ala Lys Lys Ser Met Asp Val Leu Thr Asn
225 230 235 240

Gly Arg Ala Glu Glu Leu Gly Arg Ile Lys Val Thr Tyr Glu Glu Val
245 250 255

Ala Ser Ser Leu Cys Gly Leu Lys
260

<210> SEQ ID NO 12
<211> LENGTH: 27
<212> TYPE: DNA
<213> ORGANISM: Artificial Sequence
<220> FEATURE:
<223> OTHER INFORMATION: Primer -continued

<400> SEQUENCE: 12
ccggatccat gcagttctct cacgctc 27

<210> SEQ ID NO 13
<211> LENGTH: 26
<212> TYPE: DNA
<213> ORGANISM: Artificial Sequence
<220> FEATURE:
<223> OTHER INFORMATION: Primer

<400> SEQUENCE: 13
ccgaattcag tgaaatcagg tgtgtt 26

<210> SEQ ID NO 14
<211> LENGTH: 27
<212> TYPE: DNA
<213> ORGANISM: Artificial Sequence
<220> FEATURE:
<223> OTHER INFORMATION: Primer

<400> SEQUENCE: 14
ccccagatcg tgcttgtcag ttttcgt 27

<210> SEQ ID NO 15
<211> LENGTH: 29
<212> TYPE: DNA
<213> ORGANISM: Artificial Sequence
<220> FEATURE:
<223> OTHER INFORMATION: Primer

<400> SEQUENCE: 15
gggaattctt aggtctcgga tggctcggg 29

<210> SEQ ID NO 16
<211> LENGTH: 27
<212> TYPE: DNA
<213> ORGANISM: Artificial Sequence
<220> FEATURE:
<223> OTHER INFORMATION: Primer

<400> SEQUENCE: 16
ccggatccgc tctcaactgc ttcgttg 27

<210> SEQ ID NO 17
<211> LENGTH: 29
<212> TYPE: DNA
<213> ORGANISM: Artificial Sequence
<220> FEATURE:
<223> OTHER INFORMATION: Primer

<400> SEQUENCE: 17
ggagatcttt aggtctcgga tggctcggg 29

<210> SEQ ID NO 18
<211> LENGTH: 27
<212> TYPE: DNA
<213> ORGANISM: Artificial Sequence
<220> FEATURE:
<223> OTHER INFORMATION: Primer

<400> SEQUENCE: 18
ccggatccgc tctcaactgc ttcgttg 27

-continued

<210> SEQ ID NO 19
<211> LENGTH: 27
<212> TYPE: DNA
<213> ORGANISM: Artificial Sequence
<220> FEATURE:
<223> OTHER INFORMATION: Primer

<400> SEQUENCE: 19
cccgtcgact taggtctcgg atggctc 27

<210> SEQ ID NO 20
<211> LENGTH: 165
<212> TYPE: PRT
<213> ORGANISM: Artificial Sequence
<220> FEATURE:
<223> OTHER INFORMATION: Fusion peptide

<400> SEQUENCE: 20

```
Met Ser Asp Lys Ile Ile His Leu Thr Asp Asp Ser Phe Asp Thr Asp
 1               5                  10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Asp Lys Ala Met
145                 150                 155                 160

Ala Asp Ile Gly Ser
                165
```

<210> SEQ ID NO 21
<211> LENGTH: 34
<212> TYPE: PRT
<213> ORGANISM: Artificial Sequence
<220> FEATURE:
<223> OTHER INFORMATION: Fusion peptide

<400> SEQUENCE: 21

```
Met Gly Ser Ser His His His His His His Ser Ser Gly Leu Val Pro
 1               5                  10                  15

Arg Gly Ser His Met Ala Ser Met Thr Gly Gly Gln Gln Met Gly Arg
            20                  25                  30

Gly Ser
```

<210> SEQ ID NO 22
<211> LENGTH: 10
<212> TYPE: PRT
<213> ORGANISM: Artificial Sequence
<220> FEATURE:
<223> OTHER INFORMATION: Fusion peptide -continued

<400> SEQUENCE: 22

Asp Tyr Lys Asp Asp Asp Asp Lys Glu Phe
 1               5                  10

<210> SEQ ID NO 23
<211> LENGTH: 744
<212> TYPE: DNA
<213> ORGANISM: Artificial Sequence
<220> FEATURE:
<223> OTHER INFORMATION: CSA polypeptide

<400> SEQUENCE: 23
atccttctca tcacattccc aacggatatc acgactaaga tttaatcaga acccttgaga 60
aactttctta taccttcacc tctccgacac acttcctcca taacaaaact ctaaaatcgg 120
gaaagatgaa gttctcactc ctcagcgcta tcgcagcggc tgtcttcgtc cctttcacat 180
ccgccactcc acttgctagc acggccgacc tcagctacga cactcactac gatgacccat 240
ccctgcccct gagtggcgtc acctgttctg acggggacaa tggcatgata acaaagggct 300
acaacaccgc cggcgagata ccaaactacc ctcacgtcgg aggagctttt acggtcgaaa 360
cgtggaacag ccccaactgt ggaaagtgct acaaagtgac atacaatgct aaaacgattt 420
ttttgactgc gatcgaccac agcaactccg gatttaatat cgcgaagaag tcgatggacg 480
tattgacgaa cggacgggca gaggaattgg gcaggatcaa ggtgacctac gaagaggtcg 540
cctcgtcgtt gtgcgggttg aaataaaggc gtattgggcg atgtgccgca atgctgagtg 600
cgatgatttg atatttgttt ggttgaaggg gaggaacctt aatgttaaac ggttttcttt 660
acatttgtaa tgcatgtggc gagggatata tgattactcg actggattat aatatctaat 720
gctaaatttc gaggtttatc gggg 744

<210> SEQ ID NO 24
<211> LENGTH: 20
<212> TYPE: DNA
<213> ORGANISM: Artificial Sequence
<220> FEATURE:
<223> OTHER INFORMATION: Synthetic peptide

<400> SEQUENCE: 24
tccatgacgt tcctgacgtt 20

<210> SEQ ID NO 25
<211> LENGTH: 25
<212> TYPE: DNA
<213> ORGANISM: Artificial Sequence
<220> FEATURE:
<223> OTHER INFORMATION: Primer

<400> SEQUENCE: 25
ccgaattcat gcagttctct cacgc 25

<210> SEQ ID NO 26
<211> LENGTH: 24
<212> TYPE: DNA
<213> ORGANISM: Artificial Sequence
<220> FEATURE:
<223> OTHER INFORMATION: Primer

<400> SEQUENCE: 26
ttggatccgg tctcggatgg ctcg 24

-continued

<210> SEQ ID NO 27
<211> LENGTH: 27
<212> TYPE: DNA
<213> ORGANISM: Artificial Sequence
<220> FEATURE:
<223> OTHER INFORMATION: Primer

<400> SEQUENCE: 27
cccggatcca tgaagttctc actcctc 27

<210> SEQ ID NO 28
<211> LENGTH: 25
<212> TYPE: DNA
<213> ORGANISM: Artificial Sequence
<220> FEATURE:
<223> OTHER INFORMATION: Primer

<400> SEQUENCE: 28
cccgtcgact tatttcaacc cgcac 25

<210> SEQ ID NO 29
<211> LENGTH: 27
<212> TYPE: DNA
<213> ORGANISM: Artificial Sequence
<220> FEATURE:
<223> OTHER INFORMATION: Primer

<400> SEQUENCE: 29
ccggatccat tgacatccca ccagttg 27

<210> SEQ ID NO 30
<211> LENGTH: 29
<212> TYPE: DNA
<213> ORGANISM: Artificial Sequence
<220> FEATURE:
<223> OTHER INFORMATION: Primer

<400> SEQUENCE: 30
ccgaattctt agccagtggg gacaccacc 29

<210> SEQ ID NO 31
<211> LENGTH: 26
<212> TYPE: DNA
<213> ORGANISM: Artificial Sequence
<220> FEATURE:
<223> OTHER INFORMATION: Primer

<400> SEQUENCE: 31
ccgaattcgt gcttgtcagt tttgct 26

<210> SEQ ID NO 32
<211> LENGTH: 29
<212> TYPE: DNA
<213> ORGANISM: Artificial Sequence
<220> FEATURE:
<223> OTHER INFORMATION: Primer

<400> SEQUENCE: 32
ccagatcttt agccagtggg gacaccacc 29

<210> SEQ ID NO 33
<211> LENGTH: 27
<212> TYPE: DNA
<213> ORGANISM: Artificial Sequence
<220> FEATURE:
<223> OTHER INFORMATION: Primer -continued

```
<400> SEQUENCE: 33

ccccagatcg tgcttgtcag ttttcgt                                  27


<210> SEQ ID NO 34
<211> LENGTH: 26
<212> TYPE: DNA
<213> ORGANISM: Artificial Sequence
<220> FEATURE:
<223> OTHER INFORMATION: Primer

<400> SEQUENCE: 34

ccggatccca gctcccagac atccca                                   26


<210> SEQ ID NO 35
<211> LENGTH: 28
<212> TYPE: DNA
<213> ORGANISM: Artificial Sequence
<220> FEATURE:
<223> OTHER INFORMATION: Primer

<400> SEQUENCE: 35

cgaattctta agcggcggtg gtgtcaac                                 28
```

PEPTIDES AND DNA ENCODING THE PEPTIDES USEFUL FOR IMMUNIZATIONS AGAINST *COCCIDIOIDES* SPP. INFECTIONS

RELATED APPLICATIONS

This application claims benefit of priority under 35 U.S.C. 119(B) of Provisional application 60/373,635, filed Apr. 19, 2002, the contents of which are incorporated herein by reference.

GOVERNMENT LICENSE RIGHTS

The United States Government has a paid up license in this invention and the right in limited circumstances to require the patent owner to license others on reasonable terms as provided for by the terms of PHS Research Grant No. 5 P01 A/37232-06 awarded by the National Institutes of Health.

FIELD OF THE INVENTION

The present invention relates generally to the fields of pathogenic fungi and immunology. More particularly, the present invention provides compositions of *Coccidioides* spp. peptides and polynucleotides encoding the peptides, which peptides are useful for generating or detecting an immunological response in an individual and in vaccines and therapeutic applications of infections due to pathogenic *Coccidioides* spp. fungi, such as *C. posadasii* or *C. immitis*.

BACKGROUND OF THE INVENTION

Coccidioidomycosis, otherwise known as the San Joaquin Valley Fever, is a fungal respiratory disease of humans and wild and domestic animals which is endemic to southwestern United States, northern Mexico, and numerous semiarid areas of Central and South America (Pappagianis, D. Epidemiology of Coccidioidomycosis. Current Topics in Medical Mycology. 1988. 2:199–23). Infection occurs by inhalation of airborne spores (arthroconidia) produced by the saprobic phase of *Coccidioides* spp., which grows in alkaline desert soil. *C. immitis* was the first described species, and is now becoming known as the Californian species. The *C. posadasii* species was recently defined, and was previously recognized as the non-Californian population of *C. immitis* (Fisher, M. C., Koenig, G. L., White, T. J., Taylor, J. W. Molecular and phenotypic description of *Coccidioides posadasii* sp. nov., previously recognized as the non-California population of *Coccidioides immitis*. Mycologia 2002. 94(1):73–84, 2002). The differences in the two species are slight. Morphologically they are indistinguishable and no differences in their ability to cause disease are known.

It is estimated that 100,000 new cases of this disease occur annually within the rapidly growing population of people who live in regions of the United States between southwest Texas and southern California, where the disease is endemic (Galgiani, J. N. Coccidioidomycosis: A regional disease of national importance; rethinking our approaches to its control. Annals of Internal Medicine. 1999. 130:293–300). Although the majority of immunocompetent individuals are able to resolve their *Coccidioides* spp. infection spontaneously, the level of morbidity associated even with the primary form of this respiratory mycosis warrants consideration of a vaccine against the disease. Immunocompromised patients, including those infected with human immunodeficiency virus, are at high risk to contract disseminated coccidioidomycosis (Ampel, N. M., C. L. Dols, and J. N. Galgiani. Results of a prospective study in a coccidioidal endemic area. American Journal of Medicine. 1993. 94:235–240). It is also apparent from results of several clinical studies that African-Americans and Asians are genetically predisposed to development of the potentially fatal, disseminated form of the respiratory disease (Galgiani, J. N. 1993. Coccidioidomycosis. Western Journal of Medicine 159:153–171).

The rationale for commitment of research efforts to develop a *Coccidioides* spp. vaccine is based on clinical evidence that individuals who recover from the respiratory coccidioidomycosis disease retain effective long-term cellular immunity against future infections by the pathogen (Smith, C. E. 1940. American Journal of Public Health 30:600–611). In addition, early preclinical studies demonstrated that a formalin-killed whole-cell (spherule) vaccine prevented deaths in mice after infection with even very large numbers of coccidioidal spores (Levine et al.1961. Journal of Immunology 87:218–227). However, when a similar vaccine preparation was evaluated in a human trial, there was substantial local inflammation, pain, and induration at the injection site, rendering the vaccine unacceptable (Pappagianis et al. Evaluation of the protective efficacy of the killed *Coccidioides immitis* spherule vaccine in humans. American Review of Respiratory Diseases. 1993. 148:656–660). Further, there was no difference in the number of cases of coccidioidomycosis or the severity of the disease in the formalin-killed spherule vaccinated group compared to the placebo group. Therefore, the original human vaccine trial was not successful.

Subsequent attempts to develop a coccidioidal vaccine focused on crude or partially purified subcellular preparations from the fungus, and had limited success in experimental models (Zimmermann, C. R., S. M. Johnson, G. W. Martens, A. G. White, B. L. Zimmer, and D. Pappagianis. Protection against lethal murine coccidioidomycosis by a soluble vaccine from spherules. Infection and Immunity. 1988. 66:2342–2345; Lecara, G., Cox, R. A., and Simpson, R. B. *Coccidioides immitis* vaccine: potential of an alkali-soluble, water-soluble cell wall antigen. Infection and Immunity. 1983. 39: 473–475; Cole, G. T., T. N. Kirkland, and S. H. Sun. An immunoreactive, water-soluble conidial wall fraction of *Coccidioides immitis* 1987. Infection and Immunity 55:657–667; Cole G. T., Kirkland T. N., Franco M., Zhu S., Yuan L., Sun S. H., Hearn V. M. Immunoreactivity of a surface wall fraction produced by spherules of *Coccidioides immitis*. Infection and Immunity October 1988; 56:2695–701).

There is a long felt need for a more effective and usable treatment or vaccination regimen to prevent, treat, or ameliorate infection of *Coccidioides* spp. and disease states associated with the infection.

SUMMARY OF THE INVENTION

Accordingly, it is an object herein to provide the methods for identifying and isolating polypeptides and nucleic acids encoding polypeptides of *Coccidioides* spp. that have an immunostimulatory activity. Such immunostimulatory nucleotides and polypeptides will be useful in the prevention, treatment, and diagnosis of infections due to *Coccidioides* spp.

In order to meet these needs, the present invention provides compositions and methods for the production of antigens comprising polypeptide fragments of the Ag2/PRA protein of *C. posadasii*, including but not limited to the polypeptide sequences of SEQ ID NO:4, SEQ ID NO: 5, SEQ ID NO:7, SEQ ID NO:9 and or SEQ ID NO:11.

The present invention also provides polynucleotides encoding the polypeptides, produced by recombinant technology from the Ag2/PRA gene and gene fragments derived from *Coccidioides posadasii*, including but not limited to the polynucleotide sequences of SEQ ID NO:3, SEQ ID NO:6, SEQ ID NO:8 and or SEQ ID NO:10.

In one embodiment, the polypeptide of the present invention encompasses the polypeptide sequence of amino acids 37 to 142 of SEQ ID NO:5 and or the polypeptide sequence of amino acids 21 to 126 of SEQ ID NO:9, and is referred to as Ag2/PRA1-106. In another embodiment, the present invention includes a polypeptide that lacks the corresponding N-terminal amino acids 1 to 26 of Ag2/PRA1-106 (exclusive of the amino acids of the fusion partner protein encoded by the vector), resulting in the polypeptide sequence of amino acids 35 to 114 of SEQ ID NO:7, and is referred to as Ag2/PRA27-106.

The present invention also provides the use of the Ag2/PRA1-106 and Ag2/PRA27-106 polypeptides and polynucleotides encoding the polypeptides to elicit an immune response sufficient to provide an effective immunization against *Coccidioides* spp. infection. In one embodiment, the polypeptides provide protection against *Coccidioides posadasii* and or *Coccidioides immitis* infections in a mammal, such as a human. In another embodiment, the polypeptides provide protection against *Coccidioides* spp. infection in domestic animals, including but not limited to dogs, cats, horses, and cattle. In a further embodiment, the invention provides polynucleotides encoding Ag2/PRA1-106 and or Ag2/PRA27-106 polypeptides in a vector suitable for transforming mammalian cells as a method for immunizing mammals against *Coccidioides* spp. infection.

The present invention further provides compositions and the methods of use of the above-mentioned Ag2/PRA1-106 and Ag2/PRA27-106 polypeptides in combination with one or more other *Coccidioides* spp. antigens to elicit an immune response sufficient to provide an effective immunization against *Coccidioides* spp. infection. In one embodiment the polypeptides are provided as a composition containing a mixture of said antigens, for example, Ag2/PRA1-106 and Coccidioides-immitis specific antigen (referred to hereafter as Csa), (Pan, S. and Cole, G. T. 1995. Molecular and biochemical characterization of *Coccidioides immitis*-specific (CS) antigen. Infection and Immunity, 63:3994–4002). In another embodiment the composition is provided as a single fusion polypeptide comprised of *Coccidioides* spp. antigens, for example the Ag2/PRA1-106+Csa chimeric fusion polypeptide of SEQ ID NO:11.

The invention also provides expression vectors that include regulatory sequences such as promoters or other transcriptional regulatory elements operably linked to the nucleotide sequences that control expression of the nucleotide sequences or degenerate variants of the sequences in host cells for the production of the polypeptides of SEQ ID NO:5, or SEQ ID NO:7, or SEQ ID NO:9, or SEQ ID NO:11.

The invention further provides host cells derived from yeast, bacterial, plant, animal or human sources containing the expression vectors comprising the sequences of SEQ ID NO:3 or SEQ ID NO:6 or SEQ ID NO:8 or SEQ ID NO:10.

The present invention also provides shorter polypeptide fragments included within amino acids 37 to 142 of SEQ ID NO:5 and or amino acids 55 to 136 of SEQ ID NO:5 and or amino acids 21 to 126 of SEQ ID NO:9 and or amino acids 35 to 114 of SEQ ID NO:7 and or amino acids 11 to 264 of SEQ ID NO:11, respectively. In preferred embodiments, these shorter polypeptides may include polypeptides of not less than 25 amino acids in length, inclusive of 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, and 78–100 amino acids in length. Such polypeptide fragments, which are substantially the same amino acid length as the sequences containing the antigenic epitopes, provide similar ability to elicit an immune response, including such immune responses that provides protection against *Coccidioides* spp. infection.

In another embodiment, the present invention includes polypeptides which are substantially identical to the polypeptide sequences of SEQ ID NO:5 and or SEQ ID NO:8 and or SEQ ID NO:7 and or SEQ ID NO:11 and or contain at least one conservative amino acid substitution. Such polypeptides, which are substantially the same amino acid length, provide similar ability to elicit an immune response, including such immune responses that provides protection against *Coccidioides* spp. infection. Such polypeptides, having substantial identity to the polypeptides of Ag2/PRA1-106 and or Ag2/PRA27-106, include those polypeptides at least about 99% identical or equivalent, at least about 95% identical or equivalent, at least about 90% identical or equivalent, at least about 85% identical or equivalent, at least about 80% identical or equivalent, at least about 75% identical or equivalent, and at least about 70% identical to said polypeptides and which have the aforementioned activities, are encompassed in the invention.

The present invention further provides methods and compositions of isolated polypeptides identical or substantially identical to the polypeptide sequences of SEQ ID NO:5, SEQ ID NO:9, SEQ ID NO:7 and or SEQ ID NO:11 useful in pharmaceutical compositions.

The present invention also provides vaccine formulations and methods of preparing the formulations containing the Ag2/PRA1-106 and or Ag2/PRA27-106 polypeptides and or polynucleotides encoding the polypeptides. The present invention further provides vaccine formulations containing adjuvants and pharmaceutical excipients and carriers.

The present invention provides the Ag2/PRA1-106 and or Ag2/PRA27-106 and or other *Coccidioides* spp. polypeptides as vaccine formulations and methods for eliciting an effective immune response in a mammal, including humans and domestic animals, for the prevention of *Coccidioides* spp. infections.

The present invention further provides kits containing the Ag2/PRA1-106 and or Ag2/PRA27-106 polypeptides and or other *Coccidioides* spp. antigens and or polynucleotides encoding the polypeptides, to facilitate the use of the polypeptides and or polynucleotides.

The present invention also provides a contruct comprising a promoter sequence for the Ag2/PRA1-106 and or Ag2/PRA27-106 genes encoding the polypeptides and or other *Coccidioides* spp. antigens, which can direct gene expression in a host cell.

The present invention also provides the use of the Ag2/PRA1-106 and or Ag2/PRA27-106 polypeptides and or polynucleotides encoding the Ag2/PRA1-106 and or Ag2/PRA27-106 polypeptides in diagnostic kits for the detection of infections due to *Coccidioides* spp. in mammals, such as humans and domestic animals.

The present invention also provides an antibody specific for an antigen of the Ag2/PRA1-106 and or Ag2/PRA27-106 polypeptides and methods for the creation of such antibodies. Such antibodies may be used in diagnostic kits for the detection of infections due to *Coccidioides* spp. The present invention provides kits containing antibodies in suitable compositions for the detection of infections due to *Coccidioides* spp. in mammals, such as humans and domestic animals.

The above and other aspects of the invention will become readily apparent to those of skill in the art from the following detailed description and figures, wherein only the preferred embodiments of the invention are shown and described, simply by way of illustration of the best mode of carrying out the invention. As is readily recognized, the invention is capable of modifications within the skill of the relevant art without departing from the spirit and scope of the invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1: Nucleotide (SEQ ID NO:1) and derived amino acid sequences (SEQ ID NO:2) of the cDNA *C. posadasii* Ag2/PRA gene aligned by the TRANSLATE program of the GCG Package. The translated nucleotide sequence results in a protein of 194 amino acid residues with a putative N-terminal signal sequence as the first 18 amino acids.

FIG. 2: The aligned nucleotide (SEQ ID NO:3) and deduced amino acid sequences (SEQ ID NO:4) of the recombinant Ag2/PRA1-106 gene expressed in an *E. coli* host. The translated nucleotide sequence results in a protein of 271 amino acid residues, of which 142 are retained after thrombin cleavage (SEQ ID NO:5).

FIG. 3: The aligned nucleotide (SEQ ID NO:6) and deduced amino acid sequences (SEQ ID NO:7) of the recombinant Ag2/PRA27-106 gene. The translated nucleotide sequence results in a protein of 114 amino acid residues.

FIG. 4: The aligned nucleotide (SEQ ID NO:8) and deduced amino acid sequences (SEQ ID NO:9) of the recombinant Ag2/PRA1-106 gene expressed in a *Saccharomyces cerevisiae* host. The translated nucleotide sequence results in a protein of 126 residues.

FIG. 5: Annotated diagram of full-length Ag2/PRA and subunits evaluated in experimental mouse models of coccidioidomycosis.

BRIEF DESCRIPTION OF THE SEQUENCE LISTING

SEQ ID NO:1 depicts the determined cDNA nucleotide sequence encoding full-length Ag2/PRA;

SEQ ID NO:2 depicts the deduced amino acid sequence of the full-length Ag2/PRA polypeptide encoded by the nucleotide sequence of SEQ ID NO:1;

SEQ ID NO:3 depicts the determined nucleotide sequence of the pET32a recombinant construct encoding the Ag2/PRA1-106 fusion polypeptide;

SEQ ID NO:4 depicts the deduced amino acid sequence of the recombinant Ag2/PRA1-106 fusion polypeptide, including 165 N-terminal amino acids derived from the pET32a vector, encoded by the nucleotide sequence of SEQ ID NO:3 and produced in *E. coli;*

SEQ ID NO:5 depicts the deduced amino acid sequence of the recombinant Ag2/PRA1-106 fusion polypeptide remaining after thrombin cleavage of the polypeptide of SEQ ID NO:4, including 36 N-terminal amino acids (SEQ ID NO:20) derived from the pET32a vector;

SEQ ID NO:6 depicts the determined nucleotide sequence of the pET28a recombinant construct encoding the Ag2/PRA27-106 fusion polypeptide;

SEQ ID NO:7 depicts the deduced amino acid sequence of the recombinant Ag2/PRA27-106 fusion polypeptide, including 34 N-terminal amino acids (SEQ ID NO: 21) derived from the pET28a vector, encoded by the nucleotide sequence of SEQ ID NO:5 and produced in *E. coli;*

SEQ ID NO:8 depicts the determined nucleotide sequence of the YEpFLAG-1 recombinant construct encoding the Ag2/PRA1-106 fusion polypeptide;

SEQ ID NO:9 depicts the deduced amino acid sequence of the recombinant Ag2/PRA1-106 fusion polypeptide, including 20 N-terminal amino acids (SEQ ID NO:22) derived from the YEpFLAG-1 vector, encoded by the nucleotide sequence of SEQ ID NO:8 and produced in *Saccharomyces cerevisiae;*

SEQ ID NO:10 depicts the determined nucleotide sequence of the YEpFLAG-1 recombinant construct encoding the Ag2/PRA1-106+Csa chimeric fusion polypeptide;

SEQ ID NO:11 depicts the deduced amino acid sequence of the recombinant Ag2/PRA1-106+Csa chimeric fusion polypeptide, including 10 N-terminal amino acids and two amino acids separating Ag2/PRA1-106 and Csa derived from the vector, encoded by the nucleotide sequence of SEQ ID NO:10 and produced in *Saccharomyces cerevisiae;*

SEQ ID NO:12 depicts the nucleotide sequence of the sense P1 primer used for cloning the Ag2/PRA sequence into the pET32a and pVR1020 vectors and subcloning the Ag2/PRA1-106 sequence into the pET32a, pVR1020 and YEp-FLAG-1 vectors at the BamHI restriction site;

SEQ ID NO:13 depicts the nucleotide sequence of the antisense P2 primer used for cloning the Ag2/PRA sequence into the pET32a vector at the EcoRI restriction site;

SEQ ID NO:14 depicts the nucleotide sequence of the antisense P10 primer used for cloning the Ag2/PRA sequence into the pVR1020 vector at the BglII restriction site;

SEQ ID NO:15 depicts the nucleotide sequence of the antisense P4 primer used to subclone the Ag2/PRA1-106 sequence into the pET32a vector and the Ag2/PRA27-106 sequence into the pET28a vector at the EcoRI restriction sites;

SEQ ID NO:16 depicts the nucleotide sequence of the sense P3 primer used to subclone the Ag2/PRA27-106 sequence into the pET28a vector at the BamHI restriction site;

SEQ ID NO:17 depicts the nucleotide sequence of the antisense P8 primer used to subclone the Ag2/PRA1-106 sequence into the pVR1020 vector at the BglII restriction site;

SEQ ID NO:18 depicts the nucleotide sequence of the sense P5 primer used to subclone the Ag2/PRA27-106 sequence into the pVR1020 vector at the BamHI restriction site;

SEQ ID NO:19 depicts the nucleotide sequence of the antisense P11 primer used to subclone the Ag2/PRA1-106 sequence into the YEpFLAG-1 vector at the SalI restriction site;

SEQ ID NO: 20 depicts the deduced amino acid sequence of the fusion partner peptide derived from the pET-32a vector at the N-terminal of the recombinant Ag2/PRA1-106 produced in *E. coli;*

SEQ ID NO: 21 depicts the deduced amino acid sequence of the fusion partner peptide derived from the pET-28a vector at the N-terminal of the recombinant Ag2/PRA27-106 produced in *E. coli;*

SEQ ID NO:22 depicts the deduced amino acid sequence of the fusion partner peptide derived from the YEpFLAG-1 vector at the N-terminal of the recombinant Ag2/PRA1-106 produced in *Saccharomyces cerevisiae;*

SEQ ID NO:23 depicts the determined cDNA sequence encoding the Csa polypeptide;

SEQ ID NO:24 depicts the nucleotide sequence of the synthetic CpG adjuvant used in animal experiments.

SEQ ID NO:25 depicts the nucleotide sequence of the sense P14 primer used for cloning the Ag2/PRA1-106 sequence component of the Ag2/PRA1-106+Csa chimeric construct into the YEpFLAG-1 vector at the EcoRI restriction site;

SEQ ID NO:26 depicts the nucleotide sequence of the sense P15 primer used for cloning the Ag2/PRA1-106 sequence component of the Ag2/PRA1-106+Csa chimeric construct into the YEpFLAG-1 vector at the EcoRI restriction site;

SEQ ID NO:27 depicts the nucleotide sequence of the sense P16 primer used for cloning the CSA sequence component of the Ag2/PRA1-106+Csa chimeric construct into the YEpFLAG-1 vector at the BamHI restriction site; and SEQ ID NO:28 depicts the nucleotide sequence of the sense P17 primer used for cloning the CSA sequence component of the Ag2/PRA1-106+Csa chimeric construct into the YEpFLAG-1 vector at the SalI restriction site.

SEQ ID NO:29 depicts the nucleotide sequence of the sense P5 primer used to subclone the Ag2/PRA90-151 and Ag2/PRA90-194 sequences into the pET28a vector at the BamHI restriction site;

SEQ ID NO:30 depicts the nucleotide sequence of the antisense P6 primer used to subclone the Ag2/PRA90-151 sequence into the pET28a vector at the EcoRI restriction site and the sense P6 primer used to subclone the Ag2/PRA90-194 sequence into the pVR1020 vector at the EcoRI restriction site;

SEQ ID NO:31 depicts the nucleotide sequence of the antisense P7 primer used to subclone the Ag2/PRA90-194 sequence into the pET28a vector at the EcoRI restriction site;

SEQ ID NO:32 depicts the nucleotide sequence of the antisense P9 primer used to subclone the Ag2/PRA90-151 sequence into the pET28a vector at the BglII restriction site;

SEQ ID NO:33 depicts the nucleotide sequence of the antisense P10 primer used to subclone the Ag2/PRA1-194 and Ag2/PRA90-194 sequences into the pVR1020 vector at the BglII restriction site;

SEQ ID NO:34 depicts the nucleotide sequence of the sense P12 primer used to subclone the Ag2/PRA19-100 sequence into the pET32a vector at the BamHI restriction site; and SEQ ID NO:35 depicts the nucleotide sequence of the antisense P13 primer used to subclone the Ag2/PRA19-100 sequence into the pET32a vector at the EcoRI restriction site.

DETAILED DESCRIPTION OF THE INVENTION

Although methods and materials similar or equivalent to those described herein can be used in the practice or testing of the present invention, suitable methods and materials are described herein. All publications, patent applications, patents, and other references mentioned herein are incorporated by reference in their entirety. In addition, the materials, methods, and examples are illustrative only and are not intended to be limiting.

Reference is made to standard textbooks of molecular biology that contain definitions and methods and means for carrying out basic techniques, encompassed by the present invention. See, for example, Sambrook et al., Molecular Cloning: A Laboratory Manual, Third Edition, Cold Spring Harbor Laboratory Press, New York (2001), Current Protocols in Molecular Biology, Ausubel et al (eds.), John Wiley & Sons, New York (2001) and the various references cited therein.

I. The Polypeptide Sequences of the Invention.

The invention focuses on the use of Ag2/PRA polypeptide fragments and the nucleotide sequences that encode them as immunogenic antigens for a preventative or therapeutic vaccine for coccidioidomycosis, or for detection of immune responses in individuals infected by *Coccidioides* spp.

Native Ag2/PRA is a 194 amino acid, proline-rich protein which is a component of a glycopeptide identified originally as "antigen 2" by a two-dimensional electrophoresis classification scheme (Huppert et al. 1978. Infection and Immunity 20:541–551). It contains an N-terminal signal sequence of 18 amino acids. The amino acid sequence of native Ag2/PRA is shown in SEQ ID NO:2. The genomic sequence was cloned and subsequently modified to produce select polypeptide fragments and shorter DNA vaccine constructs. The reasons for reducing the full-length antigen to fragments are multiple; 1) a positive correlation between development of DTH (delayed-type hypersensitivity) (a Th1 immune response) to coccidioidal antigens and the ability to resist disseminated coccidioidomycosis has been shown. This response is generally regarded as a MHC II type response (Louie et al. 1999. Influence of host genetics on the severity of coccidioidomycosis. Emerging Infectious Diseases 5:672–680) and that peptides that bind to MHC II receptors are generally 13–25 residues in length; 2) determination of epitopes within a larger polypeptide or multiple peptides that enhance or suppress an immune response allow for the creation of fusion polypeptides containing select epitopes that can be used as vaccines with increased potency (Sette A, et al. 2002. Optimizing vaccine design for cellular processing, MHC binding and TCR recognition. Tissue Antigens 59:443–451) and 3) reducing the size of the polypeptide can lead to desirable advantages in the production, purification and safety of a vaccine. Consequently, the full-length Ag2/PRA polypeptide sequence was evaluated and recombinant methods were used to create nucleotide sequences and polypeptides that encoded or contained regions with predicted antigenic motifs and were evaluated for their ability to elicit a protective immune response. The rAg2/PRA1-106 of the present invention is a polypeptide of 106 amino acids in length, retaining the N-terminal signal sequence of 18 amino acids found in native Ag2/PRA. In the case of the rAg2/PRA1-106 of the present invention produced in *E. coli*, it was initially expressed as a fusion polypeptide in the *E. coli* host transformed with the Ag2/PRA1-106-pET32a plasmid construct, resulting in a recombinant fusion polypeptide with 271 amino acids (SEQ ID NO:4). The aforementioned fusion polypeptide was subsequently treated with thrombin to release a polypeptide of 142 amino acids (SEQ ID NO:5), of which amino acids 37 to 142 of the sequence represent rAg2/PRA1-106 of the present invention. In the case of the rAg2/PRA1-106 of the present invention produced in *Saccharomyces cerevisiae*, it was expressed as a fusion polypeptide in the yeast host transformed with the Ag2/PRA1-106-YEpFLAG-1 plasmid construct, resulting in a recombinant fusion polypeptide with 126 amino acids (SEQ ID NO:9), of which amino acids 21 to 126 represent rAg2/PRA1-106 of the present invention.

The rAg2/PRA27-106 of the present invention is expressed as a fusion polypeptide of 114 amino acids in length, a construct designed to eliminate the N-terminal signal sequence of the native polypeptide. The amino acid sequence of the rAg2/PRA27-106 fusion polypeptide produced in the *E. coli* host transformed with the Ag2/PRA27-106-pET28a construct is shown in SEQ ID NO:7, of which amino acids 35 to 114 represent rAg2/PRA27-106 of the present invention.

Additional polypeptides are encompassed in the invention, consisting essentially of the sequences of the Ag2/PRA1-106 and or Ag2/PRA27-106 polypeptides, including polypeptides at least about 99% identical or equivalent, at least about 95% identical or equivalent, at least about 90% identical or equivalent, at least about 85% identical or equivalent, at least about 80% identical or equivalent, at least about 75% identical or equivalent, and at least about 70% identical to the sequences of the respective polypeptides.

As used herein, the terms "protein" or "polypeptide" are used in the broadest sense to mean a sequence of amino acids that can be encoded by a cellular gene or by a recombinant nucleic acid sequence or can be chemically synthesized. In some cases, the term "polypeptide" is used in referring to a portion of an amino acid sequence (peptides) of a full-length protein. An active fragment of a Ag2/PRA is an example of such a polypeptide. A protein can be a complete, full-length gene product, which can be a core protein having no amino acid modifications, or can be a post-translationally modified form of a protein such as a phosphoprotein, glycoprotein, proteoglycan, lipoprotein or nucleoprotein.

"Consisting essentially of", in relation to amino acid sequence of a polypeptide, protein or peptide, is a term used hereinafter for the purposes of the specification and claims to refer to a conservative substitution or modification of one or more amino acids in that sequence such that the tertiary configuration of the polypeptide, protein or peptide is substantially unchanged.

"Conservative substitutions" is defined by substitutions of amino acids having substantially the same charge, size, hydrophilicity, and or aromaticity as the amino acid replaced. Such substitutions, known to those of ordinary skill in the art, include glycine-alanine-valine; isoleucine-leucine; tryptophan-tyrosine; aspartic acid-glutamic acid; arginine-lysine; asparagine-glutamine; and serine-threonine.

"Modification", in relation to amino acid sequence of a polypeptide, protein or peptide, is defined functionally as a deletion of one or more amino acids which does not impart a change in the conformation, and hence the biological activity, of the polypeptide, protein or peptide sequence.

The common amino acids are generally known in the art. Additional amino acids that may be included and or substituted in the peptide of the present invention include: L-norleucine; aminobutyric acid; L-homophenylalanine; L-norvaline; D-alanine; D-cysteine; D-aspartic acid; D-glutamic acid; D-phenylalanine; D-histidine; D-isoleucine; D-lysine; D-leucine; D-methionine; D-asparagine; D-proline; D-glutamine; D-arginine; D-serine; D-threonine; D-valine; D-tryptophan; D-tyrosine; D-omithine; aminoisobutyric acid; L-ethylglycine; L-t-butylglycine; penicillamine; I-naphthylalanine; cyclohexylalanine; cyclopentylalanine; aminocyclopropane carboxylate; aminonorbornylcarboxylate; L-α-methylalanine; L-α-methylcysteine; L-α-methylaspartic acid; L-α-methylglutamic acid; L-α-methylphenylalanine; L α-methylhistidine; L-α-methylisoleucine; L-α-methyllysine; L-α-methylleucine; L-α-methylmethionine; L-α-methylasparagine; L-α-methylproline; L-α-methylglutamine; L-α-methylarginine; L-α-methylserine; L-α-methylthreonine; L-α-methylvaline; L-α-methyltryptophan; L-α-methyltyrosine; L-α-methylomithine; L-α-methylnorleucine; amino-α-methylbutyric acid;. L-α-methylnorvaiine; L-α-methylhomophenylalanine; L-α-methylethylglycine; methyl-γ-aminobutyric acid; methylaminoisobutyric acid; L-α-methyl-t-butylglycine; methylpenicillamine; methyl-α-naphthylalanine; methylcyclohexylalanine; methylcyclopentylalanine; D-α-methylalanine; D-α-methylornithine; D-α.-methylcysteine; D-α-methylaspartic acid; D-α-methylglutamic acid; D-α-methylphenylalanine; D-α-methylhistidine; D-α-methylisoleucine; D-α-methyllysine; D-α-methylleucine; D-α-methylmethionine; D-α-methylasparagine; D-α-methylproline; D-α-methylglutamine; D-α-methylarginine; D-α-methylserine; D-α-methylthreonine; D-α-methylvaline; D-α-methyltryptophan; D-α-methyltyrosine; L-N-methylalanine; L-N-methylcysteine; L-N-methylaspartic acid; L-N-methylglutamic acid; L-N-methylphenylalanine; L-N-methylhistidine; L-N-methylisoleucine; L-N-methyllysine; L-N-methylleucine; L-N-methylmethionine; L-N-methylasparagine; N-methylcyclohexylalanine; L-N-methylglutamine; L-N-methylarginine; L-N-methylserine; L-N-methylthreonine; L-N-methylvaline; L-N-methyltryptophan; L-N-methyltyrosine; L-N-methylomithine; L-N-methylnorleucine; N-amino-α-methylbutyric acid; L-N-methylnorvaline; L-N-methylhomophenylalanine; L-N-methylethylglycine; N-methyl-γaminobutyric acid; N-methylcyclopentylalanine; L-N-methyl-t-butylglycine; N-methylpenicillamine; N-methyl-α-naphthylalanine; N-methylaminoisobutyric acid; N-(2-aminoethyl)glycine; D-N-methylalanine; D-N-methylornithine; D-N-methylcysteine; D-N-methylaspartic acid; D-N-methylglutamic acid; D-N-methylphenylalanine; D-N-methylhistidine; D-N-methylisoleucine; D-N-methyllysine; D-N-methylleucine; D-N-methylmethionine; D-N-methylasparagine; D-N-methylproline; D-N-methylglutamine; D-N-methylarginine; D-N-methylserine; D-N-methylthreonine; D-N-methylvaline; D-N-methyltryptophan; D-N-methyltyrosine; N-methylglycine; N-(carboxymethyl)glycine; N-(2-carboxyethyl)glycine; N-benzylglycine; N-(imidazolylethyl)glycine; N-(1-methylpropyl)glycine; N-(4-aminobutyl)glycine; N-(2-methylpropyl)glycine; N-(2-methylthioethyl)glycine; N-(hydroxyethyl)glycine; N-(carbamylmethyl)glycine; N-(2-carbamylethyl)glycine; N-(1-methylethyl)glycine; N-(3-guanidinopropyl)glycine; N-(3-indolylethyl)glycine; N-(p-hydroxyphenethyl)glycine; N-(1-hydroxyethyl)glycine; N-(thiomethyl)glycine; N-(3-aminopropyl)glycine; N-cyclopropylglycine; N-cyclobutyglycine; N-cyclohexylglycine; N-cycloheptylglycine; N-cyclooctylglycine; N-cyclodecylglycine; N-cycloundecylglycine; N-cyclododecylglycine; N-(2,2-diphenylethyl)glycine; N-(3,3-diphenylpropyl)glycine; N-(N-(2,2-diphenylethyl)carbamylmethyl)glycine; N-(N-(3,3-diphenylpropyl)carbamylmethyl)glycine; and 1-carboxy-1-(2,2-diphenylethylamino)cyclopropane.

The polypeptides of the present invention can be produced by known chemical synthesis methods; for example, a liquid phase synthesis method, a solid phase synthesis method, and others (Izumiya, N., Kato, T., Aoyagi, H., Waki, M., Basis and Experiments of Peptide Synthesis, 1985, Maruzen Co., Ltd.).

The polypeptides of the present invention may contain one or more protected amino acid residues. The protected amino acid is an amino acid whose functional group or groups is/are protected with a protecting group or groups by a known method or by the use of various protected amino acids that are commercially available.

Because native Ag2/PRA obtained from *Coccidioides* spp. is glycosylated, the polypeptides of the present invention may be provided in a glycosylated as well as an unglycosylated form. Preparation of glycosylated protein or peptide is known in the art and typically involves expression of the recombinant DNA encoding the protein or peptide in a eukaryotic cell (e.g., yeast or mammalian). Likewise, it is generally known in the art to express the recombinant DNA encoding the protein or peptide in a prokaryotic (e.g., bacterial) cell to obtain a protein or peptide, which is not glycosylated. These and other methods of altering carbohydrate moieties on glycoproteins is found, inter alia, in Essentials of Glycobiology (1999), Edited By Ajit Varki, Cold Spring Harbor Laboratory Press, Cold Spring Harbor, N.Y., the contents of which are incorporated herein by reference.

II. The DNA Sequences of the Invention.

Alternatively, the polypeptides of the present invention can be produced by producing a polynucleotide (DNA or RNA) which encodes the amino acid sequence of a polypeptide of the present invention and producing said polypeptide by a genetic engineering technique using the polynucleotide. Polynucleotide coding sequences for amino acid residues are known in the art and are disclosed for example in Molecular Cloning: A Laboratory Manual, Third Edition, Sambrook, Fritsch, and Maniatis, Cold Spring Harbor Laboratory Press, 2001.

Analysis of genomic DNA encoding Ag2/PRA reveals an open reading frame for 194 amino acids, interrupted by two introns (GenBank Accession AF013256). The cDNA sequence encoding full-length Ag2/PRA is shown in SEQ ID NO:1 (GenBank Accession U39835). The nucleotide sequence encoding the fusion polypeptide rAg2/PRA1-106 of the present invention expressed in the *E. coli* host is comprised of 816 nucleotides, including a stop codon (SEQ ID NO:3), in a pET32a plasmid construct (Ag2/PRA1-106-pET32a). Expression of this construct results in a recombinant fusion polypeptide with 271 amino acids (SEQ ID NO:4), including 165 N-terminal fusion partner amino acids derived from the vector.

The nucleotide sequence encoding the fusion polypeptide rAg2/PRA1-106 of the present invention expressed in the *Saccharomyces cerevisiae* host is comprised of 381 nucleotides, including a stop codon (SEQ ID NO:8), in a YEp-FLAG-1 plasmid construct (Ag2/PRA1-106-YEpFLAG-1). Expression of this construct results in a recombinant fusion polypeptide with 126 amino acids (SEQ ID NO:9), including 20 N-terminal fusion partner amino acids derived from the YEpFLAG-1 vector. The nucleotide sequence encoding the fusion polypeptide rAg2/PRA27-106 of the present invention in the *E. coli* host is comprised of 345 nucleotides, including a stop codon (SEQ ID NO:6), in a pET28a plasmid construct (Ag2/PRA27-106-pET28a). Expression of this construct results in a recombinant polypeptide with 114 amino acids (SEQ ID NO:7), which includes 34 N-terminal fusion partner amino acids derived from the pET28a vector.

Within the context of the present invention "polynucleotide" in general relates to polyribonucleotides and polydeoxyribonucleotides, it being possible for these to be non-modified RNA or DNA or modified RNA or DNA. Polynucleotides which encode the peptides of the present invention mean the sequences exemplified in this application as well as those which have substantial identity to those sequences and which encode the peptides. Preferably, such polynucleotides are those which hybridize under stringent conditions as defined herein and are at least 70%, preferably at least 80% and more preferably at least 90% to 95% identical to those sequences.

"Consisting essentially of", in relation to a nucleic acid sequence, is a term used hereinafter for the purposes of the specification and claims to refer to sequences of the present invention and sequences with substitution of nucleotides as related to third base degeneracy. As appreciated by those skilled in the art, because of third base degeneracy, almost every amino acid can be represented by more than one triplet codon in a coding nucleotide sequence. Further, minor base pair changes may result in variation (conservative substitution) in the amino acid sequence encoded, which are not expected to substantially alter the biological activity of the gene product. Thus, a nucleic acid sequencing encoding a protein or peptide as disclosed herein, may be modified slightly in sequence (e.g., substitution of a nucleotide in a triplet codon), and yet still encode its respective gene product of the same amino acid sequence.

The terms "stringent conditions" or "stringent hybridization conditions" include reference to conditions under which a polynucleotide will hybridize to its target sequence, to a detectably greater degree than other sequences (e.g., at least 2-fold over background). In particular, a DNA or polynucleotide molecule which hybridizes under stringent conditions is preferably at least 70%, 75%, 80%, 85%, 90%, 95%, 97%, 98% or 99% identical to the DNA that encodes the amino acid sequences described herein. In a preferred embodiment these polynucleotides that hybridize under stringent conditions also encode a protein or peptide which upon administration to a subject provides an immunostimulation sufficient to provide some level of immune protection against *Coccidioides* spp. infection as described herein.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short polynucleotides (e.g., 10 to 50 nucleotides) and at least about 60° C. for long polynucleotides (e.g., greater than 50 nucleotides)—for example, "stringent conditions" can include hybridization in 50% formamide, 1 M NaCl, 1% SDS at 37° C., and a wash in 0.1×SSC at 60 to 65° C.

Homology, sequence similarity or sequence identity of nucleotide or amino acid sequences may be determined conventionally by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman (Advances in Applied Mathematics. 1981. 2: 482–489), to find the best segment of identity or similarity between two sequences. Gap performs global alignments: all of one sequence with all of another similar sequence using the method of Needleman and Wunsch, (Journal of Molecular Biology. 1970. 48:443–453). When using a sequence alignment program such as BestFit to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

Naturally, the present invention also encompasses DNA segments that consist essentially of or are complementary, or essentially complementary, to the sequences set forth in SEQ ID NO:3 or SEQ ID NO: 6 or SEQ ID NO:8 or SEQ ID NO:10. Nucleic acid sequences that are "complementary" are those that are capable of base-pairing according to the standard Watson-Crick complementarity rules. As used herein, the term "complementary sequences" means nucleic acid sequences that are substantially complementary, as may be assessed by the same nucleotide comparison set forth above, or as defined as being capable of hybridizing to the nucleic acid segments SEQ ID NO:3 or SEQ ID NO:6 or SEQ ID NO:8 or SEQ ID NO:10 under stringent conditions such as those described herein.

The nucleic acid segments of the present invention, regardless of the length of the coding sequence itself, may be combined with other nucleic acid and DNA sequences, such as promoters, polyadenylation signals, additional restriction enzyme sites, multiple cloning sites, other coding segments, and the like, such that their overall length may vary considerably. It is therefore contemplated that a nucleic acid segment or fragment of almost any length may be employed, with the total length preferably being limited by the ease of preparation and use in the intended recombinant protocol.

For example, nucleic acid segments or fragments may be prepared that include a short contiguous stretch identical to or complementary to the antigen encoding regions of SEQ ID NO:3 or SEQ ID NO:6 or SEQ ID NO:8 or SEQ ID NO:10, such as about a 15, 18 or 21 nucleotide stretch, up to about 20,000, about 10,000, about 5,000 or about 3,000 base pairs in length. Nucleic acid and DNA segments with total lengths of about 1,000, about 500, about 200, about 100 and about 50 base pairs in length (including all intermediate lengths) are also contemplated to be useful.

It will be readily understood that "intermediate lengths", in these contexts, means any length between the quoted ranges, such as 21, 22, 23, 24, 25, etc.; 30, 31, 32, etc.; 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; 5,000–10,000 ranges, up to and including sequences of about 12,001, 12,002, 13,001, 13,002, 15,001, 20,001 and the like.

It will also be understood that this invention is not limited to the particular nucleic acid and amino acid sequences of SEQ ID NO:3, SEQ ID NO:4, SEQ ID NO:5, SEQ ID NO:6, SEQ ID NO:7, SEQ ID NO:8, SEQ ID NO:9, SEQ ID NO:10 or SEQ ID NO:11, respectively. Recombinant vectors and isolated DNA segments may therefore variously include the coding region from SEQ ID NO:3 or SEQ ID NO: 6 or SEQ ID NO:8 or SEQ ID NO:10 coding regions bearing selected alterations or modifications in the basic coding region, or they may encode larger polypeptides that nevertheless include such coding regions or may encode biologically functional equivalent proteins or peptides that have variant amino acids sequences.

The nucleic acid and DNA segments of the present invention further include sequences that encode biologically functional equivalent *Coccidioides* spp. peptides that arise as a consequence of codon redundancy and functional equivalency that are known to occur naturally within nucleic acid sequences and the proteins thus encoded. Equally, functionally equivalent proteins or peptides may be created via the application of recombinant DNA technology in which changes in the protein structure may be engineered, based on considerations of the properties of the amino acids being exchanged. Changes designed by human intervention may be introduced through the application of site-directed mutagenesis techniques, e.g., to introduce improvements to the antigenicity of the protein.

III. Expression Vectors, Hosts, and Expression of Polypeptides of the Invention in vitro and in vivo.

The term "expression vector" refers to a polynucleotide that includes coding sequences that encode the polypeptide of the invention and provides the sequences necessary for its expression in the selected host cell. Expression vectors will generally include a transcriptional promoter and terminator, or will provide for incorporation adjacent to an endogenous promoter. Promoters that are commonly used in recombinant DNA construction include the β-lactamase (penicillinase), β-galactosidase and tryptophan (trp) promoter systems. While these are the most commonly used, other microbial promoters have been discovered and utilized, and details concerning their nucleotide sequences have been published, enabling those of skill in the art to ligate them functionally with plasmid vectors.

The recombinant host cells of the present invention may be maintained in vitro, e.g., for recombinant protein, polypeptide or peptide production. Equally, the recombinant host cells could be host cells in vivo, such as results from immunization of an animal or human with a nucleic acid segment of the invention. Accordingly, the recombinant host cells may be prokaryotic or eukaryotic host cells, such as *E. coli, Saccharomyces cerevisiae* or other yeast, mammalian or human or plant host cells. It will be further appreciated by the skilled practitioner that other prokaryotic and eukaryotic cells and cell lines may be appropriate for a variety of purposes; e.g., to provide higher expression, desirable glycosylation patterns, or other features. Expression vectors will usually be plasmids, further comprising an origin of replication and one or more selectable markers. The pET32a-Ag2/PRA1-106 construct of the present invention is an example of such expression vectors. A YEpFLAG-1-Ag2/PRA1-106 construct is another example. However, expression vectors may alternatively be viral recombinants designed to infect the host, or integrating vectors designed to integrate at a preferred site within the host's genome. Examples of other expression vectors are disclosed in Molecular Cloning: A Laboratory Manual, Third Edition, Sambrook, Fritsch, and Maniatis, Cold Spring Harbor Laboratory Press, 2001.

Such polynucleotides encoding the polypeptides of the invention and expression vectors carrying the vectors can be used to produce the polypeptides in vitro or in vivo. The polypeptides so produced can be isolated according to the procedures described herein and commonly known in the art and then used in a therapeutic or immunization protocol.

One may also prepare fusion proteins and peptides, e.g., where the *Coccidioides* spp. peptide coding region is included within the same expression unit with other proteins or peptides having desired functions, such as for purification or immunodetection purposes (e.g., proteins that may be isolated by affinity chromatography and enzyme label coding regions, respectively), or proteins and peptides encoding additional antigens capable of eliciting a second or enhanced immunostimulatory response in a subject (e.g., such as the *Coccidioides* spp. antigens Csa [SEQ ID NO:23], Gel1, Ure, or non-*Coccidioides* protein antigens or toxoids, such as tetanus toxoid, diphtheria toxoid, cholera toxoid, ovalbumin, or keyhole limpet haemocyanin).

In another embodiment, the present invention provides polynucleotide based vaccines or immune-stimulatory formulations, whereby the polynucleotide(s) encoding the polypeptides are administered directly to the subject patient in need thereof, provided the polynucleotide has the appropriate transcriptional control regions to direct the expression of the coding sequence contained in the polynucleotide or expression vector.

Therefore, the present invention also provides DNA based vaccines or immunogenic compositions to provide one or more of the polypeptides described herein. DNA vaccines have been developed for a number of diseases, whereby a DNA vaccine contains a DNA encoding an antigen cloned in a plasmid vector. It will be apparent to one skilled in the art that the immunostimulatory activity of the polypeptides encoded by the DNA sequences disclosed herein lies not in the precise nucleotide sequence of the DNA sequences, but rather in the epitopes inherent in the amino acid sequences encoded by the DNA sequences. It will therefore also be apparent that it is possible to recreate the immunostimulatory activity of one of these polypeptides by recreating the epitope, without necessarily recreating the exact DNA sequence. Such sequences may differ by reason of the redundancy of the genetic code from the sequences disclosed herein. Accordingly, the degeneracy of the genetic code further widens the scope of the present invention as it enables major variations in the nucleotide sequence of a DNA molecule while maintaining the amino acid sequence of the encoded protein or a protein that consists essentially of the same sequence. Such degeneracy is described in U.S. Pat. No. 6,228,371, the contents of which are incorporated herein by reference.

The expression of the antigen or polypeptide may be improved by providing a strong promoter such as, for example, Rous Sarcoma Virus LTR, the cytomegalovirus immediate early promoter, and the SV40 T antigen promoter. Success with DNA vaccines has been demonstrated using a variety of antigens for a number of diseases (U.S. Pat. Nos. 6,384,018, 6,284,533, 6,165,993, the contents of which are incorporated herein by reference). The DNA vaccine or immune stimulating composition may further include an acceptable carrier or liposome as described in U.S. Pat. No. 5,703,055, which is incorporated herein by reference; and can be made in accordance with known methods as described in, for example, U.S. Pat. Nos. 5,589,466; 5,580,859; 5,561,064; and 6,339,068, the contents of which are incorporated herein by reference.

The delivery of the DNA vaccine or immunostimulatory composition can be accomplished using a variety of procedures commonly employed in the art. For non-viral DNA transfer in cultured cells, examples of such methods include-calcium phosphate mediated, DEAE-dextran, electroporation, direct microinjection, liposome mediated delivery, cell sonication, and receptor mediated gene targeting which utilize a cell-receptor-specific ligand and an DNA binding agent, which mediate the uptake of a gene into a specific cell type based on the interaction of the ligand and the receptor. The recombinant DNA encoding the polypeptides of the present invention can also be provided to the cells by direct injection of the naked DNA or plasmid DNA or coupled to particle bombardment with known methods as described in, for example, U.S. Pat. No. 5,865,796, incorporated herein by reference.

In another embodied method of delivering the DNA vaccine or immunostimulatory composition to the cell, viral-vector mediated delivery can be used. Examples of viral vectors for such delivery include adeno-associated virus (AAV) (U.S. Pat. No. 5,843,742 incorporated herein by reference), adenovirus (U.S. Pat. Nos. 6,410,010 and 6,403,370, incorporated herein by reference), vaccinia virus (U.S. Pat. Nos. 6,287,570, and 6,214,353 incorporated herein by reference), herpesvirus, canarypox virus (U.S. Pat. No. 6,183,750 incorporated herein by reference), other Poxviruses, Retrovirus, and other RNA or DNA viral expression vectors known in the art.

The vectors used to deliver the polypeptides of the present invention may be maintained as an episome or stably integrated into the chromosome of the cell.

IV. How the Polypeptide may be Isolated.

The peptides and polypeptides of the present invention, when produced, can be purified by isolation and purification methods for proteins generally known in the field of protein chemistry. Within the context of the present invention, "isolated" means separated out of its natural environment. An "isolated polypeptide" is, in this context, a substantially pure polypeptide.

The term "substantially pure polypeptide" means a polypeptide that has been separated from at least some of those components which naturally accompany it, such as other contaminating polypeptides, polynucleotides, and or other biological materials often found in cell extracts. Typically, the protein is substantially pure when it is at least 60%, by weight, free from the proteins and other naturally-occurring organic molecules with which it is naturally associated in vivo. Preferably, the purity of the preparation is at least 75%, more preferably at least 90%, and most preferably at least 99%, by weight. A substantially pure Ag2/PRA polypeptide or polypeptide fragment may be obtained, for example, by extraction from a natural source, or by expression of a recombinant nucleic acid encoding an immunoreactive Ag2/PRA1-106 or Ag2/PRA27-106 polypeptide, such as the nucleic acid molecule shown as SEQ ID NO: 3 or SEQ ID NO:6, respectively, using methods described herein. In addition, an amino acid sequence consisting of at least an immunogenic portion of the amino acid sequence of SEQ ID NO: 5 or SEQ ID NO:7 or SEQ ID NO:9 or SEQ ID NO:11 can be chemically synthesized in a substantially pure form.

Methods of purification include, for example, extraction, recrystalization, ammonium sulfate precipitation, sodium sulfate, centrifugation, dialysis, ultrafiltration, adsorption chromatography, ion exchange chromatography, hydrophobic chromatography, normal phase chromatography, reversed-phase chromatography, gel filtration method, gel permeation chromatography, affinity chromatography, electrophoresis, countercurrent distribution, combinations of these, and other know protein or peptide purification methods are well known to those of skill in the art and can be used herein.

Purity can be measured by any appropriate method, e.g., HPLC analysis, immunoaffinity chromatography using an antibody specific for the Ag2/PRA polypeptide fragment, polyacrylamide gel electrophoresis, and the like.

A *Coccidioides* spp. polypeptide that is "isolated to homogeneity," as applied to the present invention, means that the *Coccidioides* spp. polypeptide has a level of purity where the *Coccidioides* spp. polypeptide is substantially free from other proteins, peptides and biological components. For example, an isolated *Coccidioides* spp. polypeptide will often be sufficiently free of other peptide and protein components so that sequencing may be performed successfully or that pharmaceutically acceptable formulations can be created. However, this does not exclude the re-mixing of the peptides of the invention, once isolated, with other vaccine components.

V. Preparation and Formulation of Vaccines.

The polypeptides and formulations employing the polypeptides may also be in the form of a peptide salt thereof. In view of the utility of the polypeptides of the present invention, preferred salts include those salts that are pharmaceutically acceptable for administration into a subject patient.

The polypeptides of the present invention may form a salt by addition of an acid. Examples of the acid include inorganic acids (such as hydrochloric acid, hydrobromic acid, phosphoric acid, nitric acid, and sulfuric acid) or organic carboxylic acids (such as acetic acid, propionic acid, maleic acid, succinic acid, malic acid, citric acid, tartaric acid, and salicylic acid), acidic sugars such as glucuronic acid, galacturonic acid, gluconic acid, ascorbic acid, etc., acidic polysaccharides such as hyaluronic acid, chondroitin sulfates, alginic acid, or organic sulfonic acids (such as methanesulfonic acid, and p-toluenesulfonic acid), etc.

The polypeptides of the present invention may also form a salt with a basic substance. Examples of these basic salts include, for example, salts with inorganic bases such as alkali metal salts (sodium salt, lithium salt, potassium salt, etc.), alkaline earth metal salts, ammonium salts, and the like or salts with organic bases, such as diethanolamine salts, cyclohexylamine salts, and the like.

In one embodiment of the present invention, the various polypeptides of the present invention may be admixed in various combinations and or admixed with other known proteins or peptides, which are known or believed to facilitate an immunological response, thereby providing protection against *Coccidioides* spp. infection. In an alternative embodiment, the polypeptides of the present invention may be administered separately, i.e., at different time points, from each or from other proteins or peptides, which are known or believed to facilitate an immunological response, thereby providing protection against *Coccidioides* spp. infection. For example, the peptide of amino acids 37 to 142 of SEQ ID NO:5 can be combined with one or more additional *Coccidioides* spp. polypeptides or antigens, such as Csa, Gel1, Ure, or non-*Coccidioides* protein antigens or toxoids, such as tetanus toxoid, diphtheria toxoid, cholera toxoid, ovalbumin (OVA), or keyhole limpet haemocyanin (KLH).

The pharmaceutically acceptable carriers which can be used in the present invention include, but are not limited to, an excipient, a stabilizer, a binder, a lubricant, a colorant, a disintegrant, a buffer, an isotonic agent, a preservative, an anesthetic, and the like which are commonly used in a medical field.

Also, the dosage form, such as injectable preparations (solutions, suspensions, emulsions, solids to be dissolved when used, etc.), tablets, capsules, granules, powders, liquids, liposome inclusions, ointments, gels, external powders, sprays, inhalating powders, eye drops, eye ointments, suppositories, pessaries, and the like, can be used appropriately depending on the administration method and the polypeptides of the present invention can be accordingly formulated. Pharmaceutical formulations are generally known in the art and are described, for example, in Chapter 25.2 of Comprehensive Medicinal Chemistry, Volume 5, Editor Hansch et al, Pergamon Press 1990.

The present invention also provides compositions containing the polypeptides or fragments thereof containing one or more suitable adjuvants commonly used in the field of immunology and medicine to enhance the immune response in a subject. Examples of such adjuvants include monophosphoryl lipid A (MPL), a detoxified derivative of the lipopolysaccharide (LPS) moiety of *Salmonella minnesota* R595, which has retained immunostimulatory activities and has been shown to promote Th1 responses when co-administered with antigens (see U.S. Pat. No. 4,877,611; Tomai et al., Journal of Biological Response Modifiers. 1987. 6:99–107; Chen et al., Journal of Leukocyte Biology 1991. 49:416–422; Garg & Subbarao. Infection and Immunity. 1992. 60(6):2329–2336; Chase et al., Infection and Immunity.1986. 53(3):711–712; Masihi et al, Journal of Biological Response Modifiers. 1988. 7:535–539; Fitzgerald, Vaccine 1991. 9:265–272; Bennett et al, Journal of Biological Response Modifiers 1988. 7:65–76; Kovach et al., Journal of Experimental Medicine, 1990. 172:77–84; Elliott et al., Journal of Immunology. 1991.10:69–74; Wheeler A. W., Marshall J. S., Ulrich J. T., International Archives of Allergy and Immunology October 2001;126(2):135–9; and Odean et al., Infection and Immunity 1990. 58(2):427–432); MPL derivatives (see U.S. Pat. No. 4,987,237) other general adjuvants (see U.S. Pat. No. 4,877,611); CpG and ISS oligodeoxynucleotides (see U.S. Pat. No. 6,194,388; U.S. Pat. No. 6,207,646; U.S. Pat. No. 6,239,116; U.S. Pat. No. 6,339,068; McCluskie, M. J., and H. L. Davis. Vaccine 2002. 19:413–422; Ronaghy A, Prakken B J, Takabayashi K, Firestein G S, Boyle D, Zvailfler N J, Roord S T, Albani S, Carson D A, Raz E. Immunostimulatory DNA sequences influence the course of adjuvant arthritis. Journal of Immunology 2002. 168(1):51–6.; Miconnet et al (2002) 168(3) Journal of Immunology pp 1212–1218; Li et al (2001) Vaccine 20(1–2):148–157; Davis (2000) Devopmental Biology 104:165–169; Derek T. O'Hagan, Mary Lee MacKichan, Manmohan Singh, Recent developments in adjuvants for vaccines against infectious diseases, Biomolecular Engineering 18 (3) (2001) pp. 69–85; McCluskie et al (2001) Critical Reviews in Immunology 21(1–3):103–120); trehalose dimycolate (see U.S. Pat. No. 4,579,945); amphipathic and surface active agents, e.g., saponin and derivatives such as QS21 (see U.S. Pat. No. 5,583,112); oligonucleotides (Yamamoto et al, Japanese Journal of Cancer Research, 79:866–873, 1988); detoxified endotoxins (see U.S. Pat. No. 4,866,034); detoxified endotoxins combined with other adjuvants (see U.S. Pat. No. 4,435,386); combinations with QS-21 (see U.S. Pat. No. 6,146,632); combinations of detoxified endotoxins with trehalose dimycolate and endotoxic glycolipids (see U.S. Pat. No. 4,505,899); combinations of detoxified endotoxins with cell wall skeleton (CWS) or CWS and trehalose dimycolate (see U.S. Pat. Nos. 4,436,727, 4,436,728 and 4,505,900); combinations of just CWS and trehalose dimycolate, without detoxified endotoxins (as described in U.S. Pat. No. 4,520,019); chitosan adjuvants (see U.S. Pat. Nos. 5,912,000; 5,965,144; 5,980,912; Seferian, P. G., and Martinez, M. L. Immune stimulating activity of two new chitosan containing adjuvant formulations (2001) Vaccine. 2000. 19(6):661–8). All of the references cited in this paragraph are incorporated herein by reference.

In another embodiment, the antigenic compositions of the present invention can be provided as an adsorbed vaccine or immunostimulatory composition as described in Matheis et al. (Matheis, M., Zott, A., Schwanig, M. 2000. The role of the adsorption process for production and control combined adsorbed vaccines. Vaccine 20:67–73), which is incorporated herein by reference.

In another embodiment, various adjuvants, even those that are not commonly used in humans, may be employed in animals where, for example, one desires to subsequently obtain activated T cells or to protect valuable or valued animals from infection due to *Coccidioides* spp.

VI. Administration of Vaccines

As used herein the subject that would benefit from the administration of the polypeptide and or nucleotide vaccines and formulations described herein include any mammal which can benefit from protection against *Coccidioides* spp. infection. In a preferred embodiment, the subject is a human. In a second embodiment, the subject is a domestic animal, including but not limited to dog, cat, horse, bovine (meaning any sex or variety of cattle) or other such domestic animals.

By polypeptides capable of eliciting an immune response in a subject human, including vaccination, the invention covers any polypeptide, peptide, peptide mimic, or chemical product capable of inducing an immune reaction that results in or augments the subject's ability to mount some level of immune protection inhibiting *Coccidioides* spp. infection. In one embodiment, the *Coccidioides* spp. is *Coccidioides immitis*. In another embodiment, the *Coccidioides* spp. is *Coccidioides posadasii.*

As used herein, "inhibit", "inhibiting" or "inhibition" includes any measurable or reproducible reduction in the infectivity of *Coccidioides* spp. in the subject patient. "Reduction in infectivity" means the ability of the subject to prevent or limit the spread of *Coccidioides* spp. fungus in tissues or organs exposed or infected by said fungus. Furthermore, "amelioration", "protection", "prevention" and "treatment" mean any measurable or reproducible reduction, prevention, or removal of any of the symptoms associated with *Coccidioides* spp. infectivity, and particularly, the prevention, or amelioration of *Coccidioides* spp. infection and resultant pathology itself.

The dosages used in the present invention to provide immunostimulation include from about 0.1 μg to about 500 μg, which includes, 0.5, 1.0, 1.5, 2.0, 5.0, 10, 15, 20, 25, 30, 35, 40, 45, 50, 55, 60, 65, 70, 75, 80, 85, 90, 95, 100, 150, 200, 250, 300, 350, 400, and 450 μg, inclusive of all ranges and subranges there between. Such amount may be administered as a single dosage or may be administered according to a regimen, including subsequent booster doses, whereby it is effective; e.g., the compositions of the present invention can be administered one time or serially over the course of a period of days, weeks, months and or years.

The polypeptide compositions of the present invention can be administered by any suitable administration method including, but not limited to, injections (subcutaneous, intramuscular, intracutaneous, intravenous, intraperitoneal), eye dropping, instillation, percutaneous administration, transdermal administration, oral administration, intranasal administration, inhalation, etc.

VII. Other Uses.

Also included within the scope of the present invention are kits suitable for providing one or more of the polypeptides of the invention. For example, in such a kit one vial can comprise the polypeptides of the invention admixed with a pharmaceutically acceptable carrier, either in a aqueous, non-aqueous, or dry state; and a second vial which can carry immunostimulatory agents, and or a suitable diluent for the peptide composition, which will provide the user with the appropriate concentration of peptide to be delivered to the subject. In one embodiment, the kit will contain instructions for using the polypeptide composition and other components, as included; such instructions can be in the form of printed, electronic, visual, and or audio instructions. The vaccinations will normally be at from two to twelve week intervals, more usually from three to five week intervals. Periodic boosters at intervals of 1–5 years, usually three years, will be desirable to maintain protective levels. The course of the immunization may be followed by assays for activated T cells produced, skin-test reactivity, or other indicators of an immune response to *Coccidioides* spp.

The polypeptide of the invention can be used to detect the presence of antibodies in the sera of patients potentially infected with *Coccidioides* spp. Antibodies that react specifically with the inventive polypeptides can be used to detect the presence of circulating antigens in the sera of patients potentially infected with *Coccidioides* spp. Such detection systems include radioimmunoassays and various modifications thereof which are well-know to those skilled in the art. In addition, the polypeptide of the invention can be used to detect the presence of a cell-mediated immune response in a biological sample. Such assay systems are also well-known to those skilled in the art and generally involve the clonal expansion of a sub-population of T cells or the production of cytokines in response to stimuli from the polypeptide or detection of reactive T cells by flow cytometry or other methods known to those skilled in the art; e.g., methods described by Richards et al. (Richards, J. O., Ampel, N. M., Galgiani, J. N. and Lake, D. F. 2001. Dendritic cells matured by *Coccidioides immitis* lysate induce antigen specific naive T cell activation. Journal of Infectious Diseases 184:1220–1224). When so-used, the humoral and or cell-mediated response of a patient can be determined and monitored over the course of the disease. Methods of generating antibodies directed to a specific peptide fragment are known in the art. Examples of such methods are disclosed in Antibodies, A Laboratory Manual, Harlow and Lane, Cold Spring Harbor Press, 1988, herein incorporated by reference.

Having generally described this invention, a further understanding can be obtained by reference to certain specific examples that are provided herein for purposes of illustration only, and are not intended to be limiting unless otherwise specified.

EXAMPLES

Example 1

Immunoprotection Studies with Recombinant Ag2/PRA Vaccines Expressed in *E. coli*

Materials and Methods

Cloning, Expression, and Characterization of Recombinant Vaccines Design of Ag2/PRA subunits. Potential antigenic domains were identified in the predicted 194 amino acid sequence of Ag2/PRA (Dugger, Kris Orsborn, Kara M. Villareal, An Ngyuen, Charles R. Zimmermann, John H. Law and John N. Galgiani. 1996. Cloning and Sequence Analysis of the cDNA for a Protein from *Coccidioides immitis* with Immunogenic Potential. Biochemical Biophysical Research Communication 218:485–489; Genbank Accession number U39835). We used the antigenicity prediction algorithm of the PEPTIDESTRUCTURE program of the GCG Package (Genetics Computer Group, Madison, Mich. [now Accelrys, San Diego, Calif.]), which analyzes six properties relating to secondary peptide structure and calculates the "antigenic index" as defined for antibody based immune responses to model proteins, and the ANTIGEN program of PC Gene (Intelligenetics, subsumed by Accelrys), which analyzes the hydrophilicity profile of polypeptides. Sequences were examined for breakpoints between high-scoring fields which were identified by both programs, and these boundaries were used as a guide in designing four overlapping subunits, corresponding to amino acids 1-40, 27-106, 90-150 and 125-194. In order to not miss epitopes, sequences were also created in which the full-length protein was divided approximately in half, separating the N-terminal cysteine motifs and C-terminal proline-threonine-rich and GPI anchor motifs, with a 17-amino acid overlap (1-106 and 90-194). Lastly, a sequence was created in which the cysteine motif was separated from the signal peptide (19-100).

Construction of plasmids. Total RNA was extracted from 48-h spherules of *C. posadasii* strain Silveira and reverse transcribed with Superscript II and oligo(dT) as previously described (Duger, K. O., Villareal, K. M., Ngyuen, A., Zimmermann, C. R., Law, J. H., and Galgiani, J. N. 1991. An immunoreactive apoglycoprotein purified from *Coccidioides immitis*. Infection and Immunity 59:2245–2251). The resulting cDNA was used as a template in a 3-step PCR process catalyzed by Pfu DNA polymerase (Stratagene, San Diego, Calif.) for 35 cycles. PCR reactions consisted of 1×Pfu buffer (10 mM KCl, 10 mM $(NH_4)_2SO_4$, 20 mM Tris-Cl pH 8.75, 2 mM $MgSO_4$, 0.1% Triton X-100 and 0.1 mg/ml BSA), 2 μl template, 0.4 mM dNTP's, and 5U Pfu polymerase. The nucleotide sequences of the sense and antisense PCR primers were 5' CCGGATCCATGCAGTTCTCTCACGCTC 3'(P1, SEQ ID NO:12) and 5'CCGAATTCAGTGAAATCAGGTGTGTT 3' (P2, SEQ ID NO:13), each of which includes a restriction site to facilitate subcloning (see Tables 1 and 2). The resulting 970 bp product encoding the full-length Ag2/PRA was gel purified, digested with BamHI and EcoRI, and ligated into the BamHI/EcoRI sites of pBluescript SK$^+$ (Stratagene) by standard techniques to create pCiAg33.41 ( J. Sambrook, E. F. Fritsch and T. Maniatis. 1989. Molecular Cloning: A Laboratory Manual, 2$^{nd}$ ed. Cold Spring Harbor Laboratory Press, Cold Spring Harbor, N.Y.).

The sequence of the cDNA insert was confirmed by automated DNA sequencing on an ABI 377 sequencer (Macromolecular Structures Facility, Arizona Research Labs, University of Arizona). The insert was excised from pBluescript with BamHI and EcoRI, and ligated into pET32a (Novagen, Madison, Wis.) to produce pPRA.B15. The orientation and frame were confirmed by sequencing, and the plasmid transformed into *E. coli* BL21(DE3)SlyD$^-$ (kind gift of Ry Young, Texas A&M University) by a $CaCl_2$ method as described (Theo N. Kirkland, Fred Finley, Kris I. Orsborn and John N. Galgiani. 1998. Evaluation of the Proline-Rich Antigen of *Coccidioides immitis* as a Vaccine Candidate in Mice. Infection and Immunity 66:3519–3522; and J. Sambrook, E. F. Fritsch and T. Maniatis. 1989. Molecular Cloning:. A Laboratory Manual, 2$^{nd}$ ed. Cold Spring Harbor Laboratory Press, Cold Spring Harbor, N.Y.). To create plasmids encoding the peptide subunits of Ag2/PRA, a series of oligonucleotide PCR primers corresponding to the desired sequences, including restriction sites for BamHI and EcoRI were designed (see Tables 1 and 2). Stop codons were included on antisense primers as appropriate. Primer pairs were used in a set of 2-step PCR reactions with pPRA.B 15 as template and Pfu DNA polymerase as above and the resulting amplimers cloned into the BamHI/EcoRI sites of pET28a (Novagen) or pET32a by standard methods (see Table 2) for expression (see Table 3).

TABLE 1

Primers used in cloning/PCR procedures

| Primer No. | SEQ ID NO: | Primer sequence* | Restiction Site Added |
|---|---|---|---|
| P1 | 12 | CCGGATCC-ATGCAGTTCTCTCACGCTC | *Bam*HI |
| P2 | 13 | CCGAATTC-AGTGAAATCAGGTGTGTT | *Eco*RI |
| P3 | 16 | CCGGATCC-GCTCTCAACTGCTTCGTTG | *Bam*HI |
| P4 | 15 | GGGAATTCTTA-GGTCTCGGATGGCTCGGG | *Eco*RI, stop |
| P5 | 29 | CCGGATCC-ATTGACATCCCACCAGTTG | *Bam*HI |
| P6 | 30 | CCGAATTCTTA-GCCAGTGGGGACACCACC | *Eco*RI, stop |
| P7 | 31 | CCGAATTC-GTGCTTGTCAGTTTTGCT | *Eco*RI |
| P8 | 17 | GGAGATCTTTA-GGTCTCGGATGGCTCGGG | *Bgl*II, stop |
| P9 | 32 | CCAGATCTTTA-GCCAGTGGGGACACCACC | *Bgl*II, stop |
| P10 | 33 | CCCCAGATC-GTGCTTGTCAGTTTTCGT | *Bgl*II |
| P11 | 19 | CCCGTCGACTTA-GGTCTCGGATGGCTC | *Sal*I, stop |
| P12 | 34 | CCGGATCC-CAGCTCCCAGACATCCCA | *Bam*HI |
| P13 | 35 | CGAATTCTTA-AGCGGCGGTGGTGTCAAC | *Eco*RI, stop |

TABLE 1-continued

Primers used in cloning/PCR procedures

| Primer No. | SEQ ID NO: | Primer sequence* | Restiction Site Added |
|---|---|---|---|
| P14 | 25 | CCGAATTC-ATGCAGTTCTCTCACGC | *Eco*RI |
| P15 | 26 | TTGGATCC-GGTCTCGGATGGCTCG | *Bam*HI |
| P16 | 27 | CCCGGATCC-ATGAAGTTCTCACTCCTC | *Bam*HI |
| P17 | 28 | CCCGTCGACTTA-TTTCAACCCGCAC | *Sal*I, stop |

*hyphen indicates interface of cDNA homology sequence and nucleotides for restriction sites, stop codons, and clamps

TABLE 2

Summary information for cloning and expression

| Expressed polypeptide/ Encoded vaccine (plasmid designation) | Primers used | Template Used | Recipient vector | Host |
|---|---|---|---|---|
| Ag2/PRA 1–194 (pPRA.B 15) | P1/P2 | cDNA | pET32a | *E. coli* |
| Ag2/PRA 27–106 | P3/P4 | pCiAg33.41 | pET28a | *E. coli* |
| Ag2/PRA 90–151 | P5/P6 | pCiAg33.41 | pET28a | *E. coli* |
| Ag2/PRA 1–106 | P1/P4 | pPRA.B15 | pET32a | *E. coli* |
| Ag2/PRA 90–194 | P5/P7 | pPRA.B15 | pET28a | *E. coli* |
| Ag2/PRA 19–100 | P12/P13 | pCVP20.17 | pET32a | *E. coli* |
| Ag2/PRA 1–194 (pCVP20. 17) | P1/P10 | pCiAg33.41 | pVR1020 | Mammalian host |
| Ag2/PRA 1–106 (pTPA) | P1/P8 | pCiAg33.41 | pVR1020 | Mammalian host |
| Ag2/PRA 90–194 (pTPB) | P6/P10 | pCiAg33.41 | pVR1020 | Mammalian host |
| Ag2/PRA 27–106 (pTP2) | P5/P8 | pCiAg33.41 | pVR1020 | Mammalian host |
| Ag2/PRA 90–151 (pTP3) | P6/P9 | PCiAg33.41 | pVR1020 | Mammalian host |
| Ag2/PRA 1–106 | P1/P11 | PCVP20.17 | YEpFLAG-1 | *S. cerevisiae* |
| Ag2/PRA 1–106 (Ag2/PRA 1–106 + Csa) | P14/P15 | PCVP20.17 | YEpFLAG-1 | *S. cerevisiae* |
| Csa (Ag2/PRA 1–106 + Csa) | P16/P17 | PET28b-CSA | YEpFLAG-1 | *S. cerevisiae* |

*full length cDNA clone

Construction of plasmid vaccines. A transcript encoding Ag2/PRA (amino acids 1-194) was cloned into the mammalian expression vector VR1020 (Vical, Inc., San Diego, Calif.). to create pCVP20.17. Briefly, the full length cDNA clone, pCiAg33.41 (Dugger et.al.1996), was used as a template with primers P1 and P2 (see Tables 1 and 2) in a two-step PCR catalyzed by Pfu DNA polymerase (Stratagene), and the resulting 615 bp amplimer ligated into the BamHI/BglII sites on pVR1020 by standard techniques to create pCVP20.17 (Abuodeh, R. O., Shubitz, L. F., Siegel, E., Snyder, S., Peng, T., Orsborn, K. I., Brummer, E., Stevens, D. A., and Galgiani, J. N. 1999. Resistance to *Coccidioides immitis* in mice after immunization with recombinant protein or DNA vaccine of a proline-rich antigen. Infection and Immunity 67:2935–2940). To make overlapping subunits in the same vector, oligonucleotide primers corresponding to the desired sequence (see FIG. 3) plus restriction sites for BamHI or BglII (see Tables 1 and 2) were used in to create sequences encoding the desired peptide fragments. The amplified fragments were cloned into the BamHI/BglII sites of VR1020 to create plasmids pTP-A (corresponding to Ag2/PRA1-106), pTP-B (corresponding to Ag2/PRA 90-194), pTP-Super2 (corresponding to Ag2/PRA19-100), pTP-2 (corresponding to Ag2/PRA 27-106) and pTP-3 (corresponding to Ag2/PRA 90-151) using the previously described methods. The orientation, frame and sequence of plasmid inserts were confirmed by DNA sequencing. DNA for use as a vaccine was prepared with the Qiagien Gigaprep kit (Chatsworth, Calif.), ethanol precipitated, and adjusted to a concentration of 1 mg/ml in phosphate buffered sterile saline and stored at −20° C. until use.

Expression and purification of recombinant peptides. Procedures for optimal expression rAg2/PRA and its subunits were developed and conditions varied individually as shown in Table 3. Growth and induction was essentially as described (Kirkland et al. 1998), with changes in medium composition and IPTG concentration as noted, except that medium for initial overnight growth of the host cells contained 10% glucose to inhibit premature expression of the polypeptides.

TABLE 3

Conditions for expression of recombinant Ag2/PRA and its subunits.

| Sequences* | Vector | Competent Cell | Medium | IPTG (mM) |
|---|---|---|---|---|
| 1–194 | PET32a | BL21(DE3)slyD- | SB | 0.5 |
| 1–106 | PET32a | BL21(DE3) | TB | 0.25 |
| 19–100 | PET32a | BL21(DE3) | LB | 0.5 |
| 90–194 | PET28a | Tuner(DE3)plysS | TB | 0.5 |
| 27–106 | PET28a | BL21(DE3)star | LB | 0.5 |

*refers to corresponding amino acid numbers of native Ag2/PRA sequence pET32 and pET28 both encode a 6×-his tag, which facilitates purification by immobilized metal affinity chromatography (IMAC). Full length Ag2/PRA was purified by batch IMAC under denaturing conditions on Ni-nitrilotriacetic acid (NTA) agarose (Qiagen, Inc., Chatsworth, Calif.) by elution with a pH step gradient essentially as described in Kirkland et. al. 1998, with the following changes. Column buffer consisted of 8M urea, 100 mM NaH2PO4, 10 mM Tris, pH 8.0 and 10% glycerol. Renaturation buffer consisted of 6.5M urea, 150 mM NaCl, 1 mM EDTA, 5 mM glutathione, 0.5 mM GSSH (oxidized glutathione), 20 mM Tris, pH 9.5 and 10% glycerol. The urea concentration of renaturation buffer was stepped down every 24 hours to 5M, 3.5M, 1M and finally 0 M urea.

Polypeptides expressed in pET32a (Ag2/PRA 1-194 and Ag2/PRA 1-106, sequence ID 4) were subjected to thrombin cleavage, to remove some vector encoded amino acids prior to final purification and use as vaccines. The fusion polypeptides were dialyzed into thrombin cleavage buffer, 20 mM Tris, pH 8.0, 150 mM NaCl and the pH adjusted to pH 8.4. $CaCl_2$ (to 2.5 mM) was added and the 6×-his tag removed by digestion with biotinylated thrombin as described (Kirkland et. al. 1998). After separation from the 6×-his tag, the protein was dialyzed into physiological buffer consisting of 5.3 mM KCl, 0.4 mM KH2PO4, 137 mM NaCl, 0.3 mM Na2HPO4 and 10 mM DTT, concentrated and quantitated.

Polypeptides expressed in pET28a (see Table 2) were not subjected to thrombin cleavage. Following step down urea dialysis, these polypeptides were dialyzed directly into physiological buffer, employing dialysis tubing and spin concentrator units with smaller molecular weight cutoffs.

The recombinant Ag2/PRA1-106 fusion polypeptide of the present invention expressed by the transformed bacterium was 271 amino acids in length and contains 165 amino acids encoded by the pET32a vector (SEQ ID NO:4). 130 amino acids, including the 6×-his tag, are removed by thrombin cleavage, leaving 36 vector-encoded and 106 Ag2/PRA1-106-encoded amino acids on the vaccine polypeptide (SEQ ID NO: 5). The recombinant Ag2/PRA27-106 fusion polypeptide of the present invention expressed by the transformed bacterium is 114 amino acids in length and contains 34 amino acids encoded by the pET28a vector and retains the 6×-his tag (SEQ ID NO:7).

Polypeptides were separated by SDS-PAGE on 12.5% polyacrylamide (Tris/glycine buffered) or 16.5% polyacrylamide (Tris/glycine buffered) gels (Bio-Rad, Hercules, Calif.), and the purity of recombinant proteins was assessed as greater than 95% by Coomassie Blue staining. Immunoblots were probed with a goat antiserum (Dugger et. al. 1996) to spherule-derived Ag2/PRA as previously described (Kirkland et al, 1998) or with anti-T7-Tag antibody conjugated to alkaline phosphatase (Novagen).

Immunization and Protection Studies

Mice. Female, 6-weeks old BALB/c mice were purchased from Harlan-Sprague-Dawley (Indianapolis, Ind.) and maintained in conventional housing under microisolation lids. Mice were immunized within one week of receipt. At the time of infection, mice were moved to Biosafety Level 3 housing where they remained for the duration of their experiment.

Immunizations. Immunization with various plasmid and recombinant peptide vaccines was carried out as previously described with groups of eight or more mice (Abuodeh R O, Shubitz L F, Siegel E, Snyder S, Peng T, Orsborn K I, Brummer E, Stevens D A, Galgiani J N. 1999 Resistance to *Coccidioides immitis* in mice after immunization with recombinant protein or DNA vaccine of a proline-rich antigen. Infection and Immunity 67:2935–40.). For DNA vaccination, mice were immunized twice 4 weeks apart with 50 µl of plasmid in various concentrations as indicated in the results injected into each cranial tibial muscle. Unimmunized control mice received the vector without insert (VR1020). For vaccination with recombinant peptides, protein suspended in 0.9% sterile saline was combined with MPL-SE adjuvant (Corixa, Inc, Hamilton, Mont.) according to the manufacturer's instructions. Mice were vaccinated twice 4 weeks apart subcutaneously in the inguinal region with 1 µg of protein per dose.

Infection. Mice were infected intraperitoneally one month after booster immunizations as previously described (Abuodeh et al., 1999), using arthroconidia of *C. immitis*, strain RS, were kindly supplied by Dr. Theo Kirkland (University of California, San Diego). For each study, viability and the size of the infecting inoculum was confirmed by plate count at the time of infection (Abuodeh et al. 1999).

Fourteen days after infection, all mice were sacrificed with an overdose of inhalant anesthesia and the right lung removed aseptically. Organs were homogenized, diluted, and plated. Colony-forming units (CFU) were enumerated at three days and reported as $Log_{10}$ CFU/organ.

Statistical analyses. For fungal burden of organs of infected animals, comparisons between groups were determined by analysis of variance (ANOVA) and Duncan's multiple range tests as implemented by SAS (SAS Institute, Inc., Cary, N.C., software version 6.12). The type I experiment-wise error rate of 0.05 was used to control for multiple comparisons.

Results

Differential effects of DNA subunit vaccines. In addition to pCVP20.17, which encodes the full-length 194-amino acid Ag2/PRA, plasmid vaccines were constructed with inserts encoding amino acid sequences 1-106, 27-106, 90-151, and 90-194 of Ag2/PRA. In two separate studies, vaccination with each of these plasmids was compared to the plasmid vector alone, using doses and conditions based on previous studies with DNA vaccines encoding full-length Ag2/PRA. As shown in Table 4, significantly fewer colonies of *Coccidioides* spp. were isolated from lungs of mice vaccinated with plasmids encoding either Ag2/PRA1-106 or Ag2/PRA27-106 than from mice receiving the vector alone. Furthermore, the plasmid encoding Ag2/PRA27-194 was less effective than the plasmid encoding full-length Ag2/PRA. In contrast, there was virtually no beneficial effect of vaccination with plasmids encoding either Ag2/PRA90-151 or Ag2/PRA90-194.

TABLE 4

Fungal burdens in lungs of mice challenged with Coccidicides spp.

| Plasmid Vaccine Group | Geometric Mean CFU* Exp. 1 | Exp. 2 |
|---|---|---|
| Vector Control | 4.92 | 4.20 |
| rAg2/PRA 90–194 | N.D. | 4.48 |
| rAg2/PRA 90–151 | 4.80 | 4.05 |
| rAg2/PRA 27–106 | 2.90 | 3.15 |
| rAg2/PRA 1–106 | 2.61 | 3.09 |
| rAg2/PRA (full length) | 2.01 | 1.94 |

*expressed as $log_{10}$ values
N.D.: not determined

Protection afforded by recombinant peptide subunit vaccines. To compare their protective efficacy as vaccines in mice, recombinant Ag2/PRA, rAg2/PRA1-106, rAg2/PRA27-106, and rAg2/PRA90-194 were expressed in *E. coli*, the polypeptides were isolated and used to immunize mice that were then challenged with *C. immitis* in a fungal burden assay. The results from quantitative cultures of the target organ lungs are shown in Table 5. As previously seen with plasmid vaccination data described above, mice vaccinated with full-length rAg2/PRA or either rAg2/PRA1-106 or rAg2/PRA27-106 of the present invention were significantly protected as compared to mice receiving adjuvant alone. Also similar to the previous study, vaccination with rAg2/PRA1-106

TABLE 5

Fungal burdens in lungs of mice challenged with Coccidicides spp.

| Group | Geometric Mean CFU* |
|---|---|
| Adjuvant Control | 5.85 |
| rAg2/PRA 90–194 | 5.69 |
| rAg2/PRA 90–151 | 2.58 |
| rAg2/PRA 27–106 + 90–194 | 3.84 |
| rAg2/PRA 27–106 | 4.25 |
| rAg2/PRA 1–106 + 90–194 | 2.58 |
| rAg2/PRA 1–106 | 2.60 |
| rAg2/PRA (full length) | 2.91 |

*expressed as $\log_{10}$ values was more protective under the conditions of the experiment than that obtained by immunization with rAg2/PRA27-106. In contrast, vaccination with rAg2/PRA90-194 showed virtually no protection and the fungal burdens were similar to those seen in the adjuvant control. Furthermore, immunization by co-administration of rAg2/PRA90-194 with either rAg2/PRA106 or rAg2/PRA27-106 did not enhance the protection obtained by immunization with the single, later recombinant polypeptides. These studies with recombinant polypeptide vaccines fully corroborate the determination of the protective antigen domain of the N-terminal 1-106 portion of the Ag2/PRA identified in the previous studies with subunit DNA vaccinations and provide strong support that the region of amino acids 90-194 does not provide any additional enhancement over that afforded by MPL adjuvant alone.

Example 2

Protection Studies with *S. cerevisiae* Expressed Ag2/PRA1-106 Polypeptide Antigen Used Singly or in Combination with a Second *Coccidioides* spp. Antigen Materials and Methods Cloning and Expression of Ag2/PRA1-106 in *Saccharomyces cerevisiae* pCVP20.17 was used as a template in a PCR catalyzed by Pfu DNA polymerase for 35 cycles as described in Example 1 above. The sense primer was P1 (5'CCGGATCCATGCAGTTCTCTCACGCT 3')(Table 1 and SEQ ID NO:12) and the antisense primer P2 (5' CCCGTCGACTTAGGTCTCGGATGGCTC 3')(SEQ ID NO:13), each of which includes a restriction site to facilitate subcloning. The resulting 338 bp product encoding the Ag2/PRA1-106 was purified using NucleoSpin Kit (Clontech, Palo Alto, Calif.), digested with BamHI and SalI, and ligated into the BamHI/SalI sites of the 7190 bp yeast expression vector YEp-FLAG-1 (Sigma, St. Louis, Mo.) using the manufacturer's protocols. The YEpFLAG-1-Ag2/PRA1-106 construct was used to transform *E. coli* DH5α by standard techniques, and clones were screened and confirmed by sequencing as described in Example 1. The YEpFLAG-1 construct was then transformed into the *S. cerevisiae* BJ3505 (Sigma, St. Louis, Mo.) host using a Yeast Transformation Kit (Sigma) by the manufacturer's protocols. Transformed yeast cells were selected by plating on Synthetic Complete Medium (SCM) minus tryptophan (Sigma).

The YEpFLAG-1-Ag2/PRA1-106+CSA chimeric construct was created using the standard methods described above. The sense and antisense primers used for the creation of the chimeric construct comprise the sequences of SEQ ID NO:25, SEQ ID NO:26, SEQ ID NO:27, and SEQ ID NO:28. The chimeric YEpFLAG-1 construct was then transformed into the *S. cerevisiae* BJ3505 (Sigma, St. Louis, Mo.) host using a Yeast Transformation Kit (Sigma) by the manufacturer's protocols. Transformed yeast cells were selected by plating on Synthetic Complete Medium (SCM) minus tryptophan (Sigma).

Recombinant protein was produced by inoculating a yeast colony from the selective agar into 30 ml of SCM minus tryptophan and growing the cells for 48–72 hours at 30° C. until the cell density reached $A_{600}$=0.6. Twenty five ml of the starter culture was added to 500 ml of YP High Stability Expression Media (Sigma) containing 1% yeast extract, 8% peptone, 1% glucose, 3% glycerol and 20 mM $CaCl_2$, and the expression culture was grown at 30° C. at 175 rpm for 96 hours. The culture supernatant containing the rAg2/PRA1-106 fusion polypeptide or the chimeric Ag2/PRA1-106+Csa fusion protein, respectively, were separated from yeast cells by centrifugation at 3000 rpm for 15 minutes.

The yeast-derived rAg2/PRA1-106 fusion polypeptide (SEQ ID NO:9) or the chimeric Ag2/PRA1-106+Csa fusion protein (SEQ ID NO:11), respectively, were purified by binding to anti-Flag-M1 Affinity Gel (Sigma) and elution with 0.1M glycine per the manufacturer's protocol. The fusion polypeptides were collected and dialyzed in physiological buffer at 4° C. and stored at −70° C. until used. Protein concentration was measured with the BCA Protein Assay Kit (Pierce, Rockford Ill.) and the purity assessed by Coomassie stain of SDS-PAGE gels and immunoblot using an anti-Ag2/PRA goat antibody as described above. Purity was further assessed by mass spectrometry, using Bruker Reflex-III MALDI/TOF (Bruker Daltonics, Billerica, Mass.). The data were analyzed with software "M over Z" (Genomic Solutions, Canada).

Mouse Immunization and Challenge Methods

Female, 6-weeks old C57B1/6 mice were purchased from Harlan-Sprague-Dawley (Indianapolis, Ind.) and maintained in conventional housing under microisolation lids. Mice were divided into four groups of 10 mice each for experimental testing of the recombinant polypeptide antigens rAg2/PRA1-106, rCsa (derived and expressed by recombinant methods from *C. posadasii* [encoded by the nucleotide sequence of SEQ ID NO:23; isolated by Dr. Garry Cole, Medical College of Ohio, Toledo, Ohio]), rAg2/PRA1-106+rCsa, or adjuvant control. For vaccination with recombinant peptides, protein was suspended in 0.9% sterile saline and combined with MPL-SE adjuvant (Corixa) and CpG, an immunostimulatory oligonucleotide sequence purchased from Integrated DNA Technologies, Inc. The CpG ODN sequence used to immunize mice was TCCAT <u>GACGTT</u>CCT<u>GACGTT</u> (SEQ ID NO:24) (CpG motifs are underlined). Mice were vaccinated twice, 14 days apart, subcutaneously in the inguinal region with 200 μl saline containing 1 μg of protein, 10 μg of CpG, and MPL-SE according to manufacturer's instructions. Controls received 10 μg CpG and MPL-SE. Animals were challenged intranasally 26 days after the last administration of antigen with 50 arthroconidia of *C. posadasii* strain Silveira. Animals were monitored for deaths for 56 days. Survivors were sacrificed with an overdose of inhalant anesthesia and the right lung removed aseptically. Organs were homogenized, diluted, and plated on agar plates for the quantitative recovery of viable *Coccidioides* spp. Colony-forming units (CFU) were enumerated at three days and reported as $Log_{10}$ CFU/organ.

Results

Mice began to look ill 14 days after challenge, with deaths ensuing thereafter. All mice in the adjuvant control group had died by Day 18 post-infection. Animals were held for a total of 56 days and the in-life portion of the experiment was terminated. The survival results are presented in Table 6. The data indicate pronounced survival in the rAg2/PRA1-106 immunized mice in comparison to those immunized with rCsa or adjuvant control. What is also apparent is the enhanced protection provided by the combination of rAg2/PRA1-106 and rCsa in comparison to the survival conferred by immunization with the single antigens alone, based both on percent survival at 56 days and mean days survived.

TABLE 6

Survival of mice challenged with *C. posadasli*

| Group | % Survival | Mean Survival (Days) |
|---|---|---|
| Adjuvant Control | 0 | 16.2 |
| rCsa | 30 | 39.7 |
| rAg2/PRA 1–106 | 60 | 42.6 |
| rAg2/PRA 1–106 + rCsa | 90 | 52.2 |

The surviving mice were euthanized on Day 56 post-infection and the lungs were removed and processed for the recovery and enumeration of the fungal burden in this target organ. The results of the quantitative cultures are presented in Table 7. To normalize the results across experimental groups, lungs from mice not surviving to Day 56 were assigned a fungal burden value of $5.0\times10^6$ cfu; a value that is twice the level possible to detect under the conditions of the experiment.

TABLE 7

Fungal burdens in lungs of mice challenged with Coccidicides spp.

| Group | Geometric Mean CFU* |
|---|---|
| Adjuvant Control | 6.70 |
| rCsa | 5.85 |
| rAg2/PRA 1–106 | 4.56 |
| rAg2fPRA 1–106 + rCsa | 3.92 |

*expressed as $\log_{10}$ values

Closely reflecting the pattern observed among survival of the vaccine groups, the fungal burdens of the mice immunized with the single antigen rAg2/PRA1-106 were reduced in comparison to those immunized with rCsa alone or in animals receiving the adjuvant control. The results of the fungal burden assay parallel those of the survival experiment in that the fungal burdens were further reduced in the group immunized by the combination of rAg2/PRA1-106 and rCsa in comparison to the survival conferred by immunization with the single antigens alone. The results thereby demonstrate the ability of the single recombinant protein rAg2/PRA1-106 to serve as an effective immunizing vaccine, and that the protection can be further enhanced by the addition of a second *Coccidioides* spp. antigen; in this case rCsa. The data also provide evidence that the yeast-derived rAg2/PRA1-106 polypeptide produces a protective immune response comparable to that seen with the comparable *E. coli*-derived polypeptide.

Example 3

Ex-vivo Production of Interferon-Gamma in Response to Single and Combination Antigen Vaccines Materials and Methods Female, 17-weeks old C57B1/6 mice were purchased from Harlan-Sprague-Dawley (Indianapolis, Ind.) and maintained in conventional housing under microisolation lids. Mice were divided into groups of 3 animals each for experimental testing of the recombinant polypeptide antigens rAg2/PRA1-106 (yeast-derived), rCsa (obtained from Dr. Garry Cole), rAg2/PRA1-106+rCsa, or adjuvant controls. For vaccination with recombinant peptides, the protein was suspended in 0.9% sterile saline and was combined with a mixture of 10 μg of CpG and 25 μg of MPL (Corixa, Inc., Hamilton, Mont.) adjuvants. Mice were vaccinated twice 14 days apart subcutaneously in the inguinal region with doses of 1 μg of protein of each antigen or control adjuvants in a volume of 200 μl. Thirty-seven days after the last immunization, mice were euthanized and spleens were aseptically removed from animals, processed and placed in cell culture media as described previously [Abuodeh et al., 1999]. Cells from each experimental group were stimulated with 10 μg/ml of each of the following: bovine serum albumin (BSA) as negative control, Concanavalin A (Con A) as positive control, rAg/PRA1-106 polypeptide, or rCsa polypeptide. After stimulation for approximately 72 h, supernatants were removed and assayed for the production of interferon gamma (IFN-γ), a key immunologic marker of a Th1 response, using an OptEIA kit (Pharmingen, Inc., San Diego, Calif.) according to the manufacturer's protocols.

Results

The results of the INF-γ assay are presented in Table 8. The positive and negative controls provided IFN-γ responses consistent with expectations. Stimulation of cells with the homologous antigens also resulted in marked responses, while stimulation with the heterologous antigens did not result in the release of detectable IFN-γ, a key immunologic marker of a Th1 response. The data indicate that vaccination of mice with

TABLE 8

Production of IFN-γ from cells obtained from immunized mice and stimulated with recombinant *C. posadasii* polypeptide antigens

| Immunizing | IFN-γ(pg/ml) from Stimulus | | | |
|---|---|---|---|---|
| Antigen | BSA | Con A | rAg2/PRA 1–106 | rCsa |
| Adjuvant Control | ND* | 6,228 | ND | ND |
| rCsa | NP | 3,611 | ND | 652 |
| rAg2/PRA 1–106 | ND | 13,120 | 5,070 | ND |
| rAg2/PRA 1–106 + rCsa | NP | 20,000 | 22,419 | 1,496 |

*Not detected: less than 125 pg/ml the recombinant *Coccidioides* spp. polypeptides leads to an immunized state that can be detected by production of the cytokine IFN-γ in response to ex vivo stimulation of spleenic cells by the antigens. There was also a markedly enhanced response to stimulation by each of the single antigens in the cells from the mice immunized by the combination of rAg2/PRA1-106+rCsa in comparison to the responses from mice immunized with the single antigens. The data suggest that immunization with the two *C. posadasii* antigens in combination may result in an additive response, as measured by IFN-γ.

Obviously, numerous modifications and variations on the present invention are possible in light of the above teachings. It is therefore to be understood that within the scope of the appended claims, the invention may be practiced otherwise than as specifically described herein.

What is claimed is:

1. An isolated polypeptide encoded by the nucleotide sequence of nucleotides 31 to 795 of SEQ ID NO:10, or an isolated polypeptide comprising the amino acid sequence of amino acids 11 to 264 of SEQ ID NO:11.

2. A composition comprising the isolated polypeptide of claim 1.

3. The composition of claim 2, wherein said composition includes a pharmaceutically acceptable carrier.

4. The composition of claim 2, further including an adjuvant.

5. The composition of claim 2, further comprising at least a second polypeptide.

6. A method of generating an immune response in a mammal, comprising introducing into the mammal a composition comprising the isolated polypeptide of claim 1, in an amount sufficient to elicit an immune response.

7. The method of claim 6 wherein said mammal is a human.

8. The method of claim 6 wherein said mammal is an animal selected from the group consisting of dog, cat, horse and bovine.

9. A method of generating antibodies that recognize the isolated polypeptide of claim 1 comprising introducing into a mammal a composition comprising the isolated polypeptide of claim 1, in an amount sufficient to elicit an antibody response.

10. The method of claim 9 wherein said mammal is a human.

11. The method of claim 9 wherein said mammal is an animal selected from the group consisting of dog, cat, horse, goat, rat, mouse, rabbit and bovine.

12. A method of generating antibodies that recognize the isolated polypeptide of claim 1 comprising introducing into a mammal a composition comprising the isolated polypeptide of claim 1 and a pharmaceutically acceptable carrier, in an amount sufficient to elicit an antibody response.

13. A method of generating antibodies that recognize the isolated polypeptide of claim 1 comprising introducing into a mammal a composition comprising the isolated polypeptide of claim 1 and an adjuvant, in an amount sufficient to elicit an antibody response.

14. A kit, comprising the isolated polypeptide of claim 1.

15. The kit of claim 14, further including an adjuvant.

16. The kit of claim 14, further including instructions for use.

17. The method of claim 6, wherein said composition further includes a pharmaceutically acceptable carrier.

18. The method of claim 6, wherein said composition further includes an adjuvant.

* * * * *